United States Patent [19]
Nissen et al.

[11] Patent Number: 5,628,328
[45] Date of Patent: May 13, 1997

[54] METHOD FOR MEASURING MUSCLE MASS

[75] Inventors: Steven L. Nissen, Ames; John A. Rathmacher, Nevada, both of Iowa; Paul J. Flakoll, Old Hickory, Tenn.

[73] Assignees: Iowa State University Research Foundation, Ames, Iowa; Vanderbilt University, Nashville, Tenn.

[21] Appl. No.: 428,052

[22] Filed: Apr. 25, 1995

[51] Int. Cl.$^6$ .................................................. A61B 5/103
[52] U.S. Cl. .................................................. 128/774
[58] Field of Search ..................................... 128/774, 782

[56] References Cited

U.S. PATENT DOCUMENTS

| | | | |
|---|---|---|---|
| 4,144,763 | 3/1979 | Vogelman | 73/433 |
| 4,184,371 | 1/1980 | Brachet | 73/433 |
| 4,616,658 | 10/1986 | Shell et al. | 128/691 |
| 4,699,887 | 10/1987 | Abbott et al. | 436/70 |
| 5,105,825 | 4/1992 | Dempster | 128/774 |
| 5,209,919 | 5/1993 | Turteltaub et al. | 424/1.1 |

OTHER PUBLICATIONS

Abumrad, N.N. et al., "Use of a Heated Superficial Hand Vein as an Alternative Site for the Measurements of Amino Acid Concentrations and for the Study of Glucose and Alanine Kinetics in Man," Metabolism (1981) 30:936–940.
Bates, P.C. et al., "Myofibrillar protein turnover: synthesis of protein–bound 3–methylhistidine, actin, myosin heavy chain and aldolase in rat skeletal muscle in the fed and starved states," Biochem. J. (1983) 214:593–605.
Berman, M. and Weiss, M.F., SAAM Manual, US Department of HEW Publication No. (NIH) 78–180. US GPO, Washington, D.C. (1978).
Blackburn, G.L. et al., "Nutritional and metabolic assessment of hospitalized patients," J. Parenter. Enteral. Nutr. (1977) 1:11–22.
Brenner, U. et al. (1987), "Der Einfluss des Dunndarms auf den 3–Methylhistidin–staffwechsel des Menschen (The effect of the small intestine on 3–methylhistidine metabolism in the human)", Infusionther. Klin. Ernahr. 14:248–251.
Brenner, U. et al., "The contribution of small gut to the 3–methylhistidine metabolism in the adult rat," Metabolism (1987) 36:416–418.
Carraro, F. (1990), "Effect of exercise and recovery on muscle protein synthesis in human subjects," Am. J. Physiol. 259E470–476.

(List continued on next page.)

*Primary Examiner*—Max Hindenburg
*Attorney, Agent, or Firm*—Greenlee, Winner and Sullivan, P.C.

[57] ABSTRACT

A method for determining muscle mass in a human subject useful for monitoring athletic conditioning, weight loss programs, nutritional deficiencies, and disease states which cause muscle wasting is provided comprising administration of a bolus dose of a metabolic marker for 3-methylhistidine, the use of a three-compartment model to describe data from blood samples collected periodically thereafter, and calculation of muscle mass as a function of specific values generated by the model.

20 Claims, 5 Drawing Sheets

OTHER PUBLICATIONS

Cobelli, et al., "Models to interpret kinetic data in stable isotope tracer studies," Am. J. Physiol. (Endrocrinol. Metab.) (1987) 253:E551–E564.

Cobelli, C. and Toffolo, G., "Compartmental versus non-compartmental modeling for two accessible pools," Am. J. Physiol. (Endocrinol. Metab.) 247: R488–R496, 1984.

Goldman, R.F. and Buskirk, E.R., "Body volume measurement by underwater weighing: description of a method", In: *Techniques for Measuring Body Composition*, J. Brozek (Ed.), Washington, D.C.: Nat'l Academy of Sciences (1961), 78–79.

Goodman, M.N., "Differential effects of acute changes in cell Ca2+ concentration on myofibrillar and non-myofibrillar protein breakdown in the rat extensor digitorum longus muscle in vitro: Assessment by production of tyrosine and N-tau-methylhistidine," Biochem. J. (1987) 241:121–127.

Goodman, M.N. and Gomez, M.D.P., "Decreased myofibrillar proteolysis after refeeding requires dietary protein or amino acids," Am. Physiological Soc. (1987), pp. E52–E58.

Harris, C. I. and G. Milne, "The urinary excretion of Nt-methyl histidine in sheep: an invalid index of muscle protein breakdown," Br.J.Nutr. (1980) 44: 129–140.

Harris, C.I. and Milne, G., "The urinary excretion of N-tau-methyl histidine by cattle: validation as an index of muscle protein breakdown," Br. J. Nutr. (1981) 45:411–422.

Harris, C. I. and G. Milne, "The inadequacy of urinary (N-tau)-methyl histidine excretion in the pig as a measure of muscle protein breakdown," Br.J.Nutr. (1981) 45:423–429.

Harris, C.I. et al., "3-Methylhistidine as a measure of skeletal-muscle protein catabolism in the adult New Zealand white rabbit," Biochem. Soc. Trans. (1977) 5:706–708.

Harris, C.I. and Milne, G., "The identification of the N-methyl histidine-containing dipeptide, balenine, in muscle extracts from various mammals and the chicken," Comp. Biochem. Physiol. (1987) 86B(2):273–279.

Haverberg, L.N. et al., "Nt-Methylhistidine content of mixed proteins in various rat tissues," Biochem. Biophys. Acta (1975) 405:67–71.

Horswill, C.A. et al., "Total-body electrical conductivity (TOBEC): relationship to estimates of muscle mass, fat-free weight, and lean body mass," Am. J. Clin. Nutr. (1989) 49:593–598.

Johnson, P. et al., "3-Methylhistidine in actin and other muscle proteins," Biochem. J. (1967) 105:361–370.

Jones, R.H. et al., "Statistical identification of compartmental models with application to plasma protein kinetics," Comp. Biomed. Res. (1984) 17:277–288.

Link, G.A. (1991), "A comprehensive approach to describing protein turnover in lambs," Ph.D. thesis, Department of Animal Science, Iowa State University.

Lohman, T.G. et al., "Bone mineral measurements and their relation to body density in children, youth and adults," Hum. Biol. (1984) 56:667–679.

Long, C.L. et al., "Metabolism of 3-methylhistidine in man," Metabolism (1975) 24:929–935.

Lowell, B.B. et al., "Regulation of myofibrillar protein degradation in rat skeletal muscle during brief and prolonged starvation," Metabolism (1986) 35:1121–1127.

Lowell, B.B. et al., "Evidence that lysosomes are not involved in the degradation of myofibrillar proteins in rat skeletal muscle," Biochem. J. (1986) 234:237–240.

Lukaski, H. C. et al., "Relationship between endogenous 3-methylhistidine excretion and body composition," Am. J. Physiol. (Endocrinol. Metab.)(1981) 240(3):E302–E307.

Lukaski, H.C. and Mendez, J., "Relationship between fat-free weight and urinary 3-methylhistidine excretion in man," Metabolism (1980) 29:758–761.

Mendez, J. et al., "Fat-free mass as a function of maximal oxygen consumption an 24-hour urinary creatinine, and 3-methylhistidine excretion," Am. J. Clin. Nutr. (1984) 39:710–714.

Millward, D.J. et al., "Quantitative importance of non-skeletal-muscle sources of N-tau-methyl-histidine in urine," Biochem. J. (1980) 190:225–228.

Millward, D. J. and P. C. Bates, "3-Methylhistidine turnover in the whole body, and the contribution of skeletal muscle and intestine to urinary 3-methylhistidine excretion in the adult rat," Biochem. J. (1983) 214:607–615.

Nishizawa, M. et al., "Fractional catabolic rates of myosin and actin estimated by urinary excretion of N-methyl histidine: the effect of dietary protein level on catabolic rates under conditions of restricted food intake," Br. J. Nutr. (1977) 37:345–353.

Pencharz, P.B. et al., "The effect of an energy-restricted diet on the protein metabolism of obese adolescents: nitrogen-balance and whole-body nitrogen turnover," Clin. Sci. (1980) 59:13–18.

Rathmacher, J.A., "Comparative evaluation of muscle proteolysis by a compartmental model of 3-methylhistidine," Ames:Ph.D. Thesis, Iowa State University, 1994.

Rathmacher, J.A. et al., "A compartmental model of 3-methylhistidine metabolism in humans," Am. Physiological Soc. (1995), pp. E193–E198.

Rathmacher, J.A. et al., "Estimation of 3-methylhistidine production in swine by compartmental analysis," Ann. Meeting Animal Sci. & International Soc. of Applied Ethology (Aug. 1992) abstract.

Rathmacher, J.A. et al., "Relationship between de novo 3-methylhistidine metabolism and body composition in pigs," J. Anim. Sci (1995).

Rathmacher, J.A. et al., "A compartmental model to measure 3-methylhistidine production in dogs following surgery," J. Nutr. (1994).

Rathmacher, J. et al., "The use of compartmental models of 3-methylhistidine flux to evaluate skeletal muscle protein turnover in implanted steers," J. Anim. Sci. (1993) 71:135 (Abstract).

Rathmacher, J.A. et al., "Technical Note: The use of a compartmental model to estimate the de novo production rate of Nt-methylhistidine in cattle," J. Anim. Sci. (1992) 70:2104–2108.

Rathmacher, J.A. et al., "Measurement of 3-methylhistidine production in lambs by using compartmental-kinetic analysis," Br. J. Nutr. (1992) 69:743–755.

Rathmacher, J.A. et al., "Estimation of 3-methylhistidine production in swine by compartmental analysis," J. Anim. Sci. (1992) Abstract, 70:194.

Rathmacher, J.A., et al., "Gas chromatographic-mass spectrometric analysis of stable isotopes of 3-methylhistidine in biological fluids: application to plasma kinetics in vivo," Biol. Mass Spectrom. (1992) 21:560–566.

Sjolin, J. et al., "Urinary excretion of 1-methylhistidine: A qualitative indicator of exogenous 3-methylhistidine and intake of meats from various sources," Metabolism (1987) 36:1175–1184.

Sjolin, J. et al., "Exchange of 3-methylhistidine in the splanchnic region in human infection," Am. J. Clin. Nutr. (1989) 50:1407–1414.

Sjolin, J. et al., "Total and net muscle protein breakdown in infection determined by amino acid effluxes," Am. J. Physiol. (Endocrinol. Metab.) (1990) 258:E856–E863.

Wolfe, R., "Radioactive and stable isotopes tracers in biomedicine: Principles and practice of kinetic analysis," New York: Wiley–Liss (1992) pp. 145–165.

Young, V. R. and H. N. Munro, "Nt-Methylhistidine (3-methylhistidine) and muscle protein turnover: an overview," Fed. Proc. (1978) 37:2291–2300.

Young, V.R. et al, "Metabolism of administered 3-methylhistidine: Lack of muscle transfer ribonucleic acid charging and quantitative excretion as 3-methylhistidine and its N-acetyl derivative," J. Biol. Chem. (1972) 217:3592–3600.

METHOD FOR MEASURING MUSCLE MASS

This invention was made, at least in part, with funding from the National Institutes of Health (Grants DK-26657, DK-20593, RR-00095 and DK-43290) and the United States Government may have certain rights therein.

FIELD OF THE INVENTION

This invention concerns the field of medicine and athletics and involves the administration of a metabolic marker for 3-methylhistidine to a subject, measurement of plasma concentration of marker and 3-methylhistidine over time, and use of these measurements to calculate muscle mass by means of a 3-compartment mathematical model.

BACKGROUND OF THE INVENTION

Techniques to measure body composition are numerous and include measurements based on: total body water, total body potassium, urinary creatinine excretion, underwater weighing (Goldman, R. F. and Buskirk, E. R., "Body volume measurement by underwater weighing: description of a method", In: *Techniques for Measuring Body Composition*, J. Brozek (ed.), Washington, D.C.: Nat'l Academy of Sciences (1961), 78–79; Lohman, T. G. et al., "Bone and mineral measurements and their relation to body density in children, youth and adults," Hum. Biol. (1984) 56:667–679), and neutron activation analysis conductivity and bioelectrical impedance (Wolfe, R., "Radioactive and stable isotopes tracers in biomedicine: Principles and practice of kinetic analysis," New York: Wiley-Liss (1992) p. 145–165). Of the current methods available to measure body composition, estimates are made of fat and fat free mass (FFM). None of the current body composition methods estimate muscle mass directly. All the methods relate back to underwater weighing which is in turn related to previous limited dissection of muscle in human cadavers. Also, such tests only estimate lean tissue, which includes bone, liver and skin.

There is great interest in the athletic population in accurately knowing muscle mass. There is also a need for an accurate method for measurement of muscle mass in order to monitor medical conditions such as nutritional deficiencies and wasting diseases.

There have been many models proposed to measure in vivo amino acid/protein kinetics. Associated with each model are both theoretical and practical problems that must be addressed. Noncompartmental models are widely used but are limited greatly by the necessary assumption that production does not occur in the sampling compartment into which the tracer is administered (Cobelli, C. and G. Toffolo. Compartmental versus noncompartmental modeling for two accessible pools. Am. J. Physiol. (Endocrinol. Metab.) 247: R488–R496, 1984). In contrast, compartmental modeling requires certain physiological assumptions, generally assigning compartments to model various components of a metabolic system. The model is constructed from an understanding of the metabolic system under study and is developed based on relationships between mathematical functions describing the isotopic decay curve and the metabolic system (Wolfe, R., "Radioactive and stable isotopes tracers in biomedicine: Principles and practice of kinetic analysis," New York:Wiley-Liss (1992) 145–165).

3-Methylhistidine has been used as a noninvasive marker of muscle proteolysis in vivo (Young, V. R. and H. N. Munro, "Nt-Methylhistidine (3-methylhistidine) and muscle protein turnover: an overview," Fed. Proc. (1978) 37:2291–2300). The primary sequence of actin and myosin white fibers in skeletal muscle contain the unique amino acid 3-methylhistidine (Johnson, P. et al., "3-Methylhistidine in actin and other muscle proteins," Biochem. J. (1967) 105:361–370). Following degradation of muscle proteins, free 3-methylhistidine is released. Yet, 3-methylhistidine is not reutilized for protein synthesis because it does not have a specific tRNA (Young, V. R. et al, "Metabolism of administered 3-methylhistidine: Lack of muscle transfer ribonucleic acid charging and quantitative excretion as 3-methylhistidine and its N-acetyl derivative," J. Biol. Chem. (1972) 217:3592–3600). 3-Methylhistidine is quantitatively excreted in the urine of man, rat, cattle and rabbit (Long, C. L. et al., "Metabolism of 3-methylhistidine in man," Metabolism (1975) 24:929–935; Young, V. R. et al., "Metabolism of administered 3-methylhistidine: Lack of muscle transfer ribonucleic acid charging and quantitative excretion as 3-methylhistidine and its N-acetyl derivative," J. Biol. Chem. (1972) 217:3592–3600; Harris, C. I. and Milne, G., "The urinary excretion of N-tau-methyl histidine by cattle: validation as an index of muscle protein breakdown," Br. J. Nutr. (1981) 45:411–422; Harris, C. I. et al., "3-Methylhistidine as a measure of skeletal-muscle protein catabolism in the adult New Zealand white rabbit," Biochem. Soc. Trans. (1977) 5:706–708). Therefore, it is thought to be a marker of skeletal muscle protein breakdown.

Urine 3-methylhistidine estimation of muscle proteolysis depends on quantitative collection and accurate measurement of urinary 3-methylhistidine. It is assumed that no metabolism of 3-methylhistidine occurs in vivo, which is true in most species (Harris, C. I. and Milne, G., "The identification of the N-methyl histidine-containing dipeptide, balenine, in muscle extracts from various mammals and the chicken," Comp. Biochem. Physiol. (1987) 86B(2):273–279). However, in the rat 3-methylhistidine is transported to liver and is acetylated. The N-acetyl-3-methylhistidine is the major form excreted in the rat (Young, V. R. et al., "Metabolism of administered 3-methylhistidine: Lack of muscle transfer ribonucleic acid charging and quantitative excretion as 3-methylhistidine and its N-acetyl derivative," J. Biol. Chem. (1972) 217:3592–3600), whereas in the adult human, N-acetyl-3-methyl-histidine accounts for less than 5% of the daily 3-methylhistidine excreted (Long, C. L. et al., "Metabolism of 3-methylhistidine in man," Metabolism (1975) 24:929–935). In sheep (Harris, C. I. and G. Milne, "The urinary excretion of Nt-methyl histidine in sheep: an invalid index of muscle protein breakdown," Br.J.Nutr. (1980) 44: 129–140) and pigs (Harris, C. I. and G. Milne, "The inadequacy of urinary (N-tau)-methyl histidine excretion in the pig as a measure of muscle protein breakdown," Br.J.Nutr. (1981) 45:423–429) 3-methylhistidine is not quantitatively excreted in urine but is retained in muscle as a dipeptide balenine (Harris, C. I. and G. Milne, "The identification of the N-methyl histidine-containing dipeptide, balenine, in muscle extracts from various mammals and the chicken," Comp. Biochem. Physiol. (1987) 86B(2):273–279). Hence, urinary 3-methylhistidine excretion cannot be used to estimate muscle protein breakdown in these species.

A compartmental model for swine or sheep must include a compartment for 3-methylhistidine metabolism other than excretion into a urine compartment. Swine excrete less than 2% of 3-methylhistidine from muscle metabolism into the urine with the majority being retained in muscle as the dipeptide balenine. Therefore, swine not only have a large pool of free 3-methylhistidine in muscle but also a large metabolic "sink" of 3-methylhistidine in the form of balenine. Likewise, sheep excrete approximately 15% of 3-methylhistidine in the urine with the remainder being retained in muscle as the dipeptide balenine. Hence a compartmental model describing the metabolism of 3-methylhistidine in these two species must incorporate these metabolic differences as compared to humans, cattle, rats and rabbits. Although there is a substantial body of literature on the metabolism of 3-methylhistidine, few reports have actually measured daily variability of endogenous 3-methylhistidine excretion. Lukaski et al. (Lukaski, H. C. et al., "Relationship between endogenous 3-methylhistidine excretion and body composition," Am. J. Physiol. (Endocrinol. Metab.)(1981) 240(3):E302–E307) reported an intra-individual coefficient of variation of 4.5% (range 2.2 to 7.0%). Similar intra-individual variation (5%) was reported by Sjolin et al. (Sjolin, J. et al., "Urinary excretion of 1-methylhistidine: A qualitative indicator of exogenous 3-methylhistidine and intake of meats from various sources," Metabolism (1987) 36:1175–1184), whereas interindividual variation (20%) is usually of a much higher magnitude even with large and homogeneous subject populations (Sjolin, J. et al., "Urinary excretion of 1-methylhistidine: A qualitative indicator of exogenous 3-methylhistidine and intake of meats from various sources," Metabolism (1987) 36:1175–1184).

A relationship between fat free mass and urinary 3-methylhistidine has been demonstrated in humans (Lukaski, H. C. and Mendez, J., "Relationship between fat-free weight and urinary 3-methylhistidine excretion in man," Metabolism (1980) 29:758–761; Lukaski, H. C. et al., "Relationship between endogenous 3-methylhistidine excretion and body composition," Am. J. Physiol. (Endocrinol. Metab.) (1981) 240(3):E302–E307; Mendez, J. et al., "Fat-free mass as a function of maximal oxygen consumption and 24-hour urinary creatinine, and 3-methylhistidine excretion," Am. J. Clin. Nutr. (1984) 39:710–714). Urinary creatinine has been suggested as an index of muscle mass and strong correlations have been demonstrated between urinary creatinine and 3-methylhistidine excretion (r=0.87, P<0.001) and between urinary creatinine and muscle mass (Lukaski, H.C. et al., "Relationship between endogenous 3-methylhistidine excretion and body composition," Am. J. Physiol. (Endocrinol. Metab.) (1981) 240(3):E302–E307). Previous studies have attempted to validate the quantitative urinary excretion of 3-methylhistidine. $^{14}$C-labeled 3-methylhistidine was injected, but its isotopic dilution was not described (Long, C. L. et al., "Metabolism of 3-methylhistidine in man," Metabolism (1975) 24:929–935).

There is a controversy as to whether urinary 3-methylhistidine is primarily a product of skeletal muscle protein turnover or whether other tissues might contribute a significant amount to the daily production. Haverberg et al. (Haverberg, L. N. et al., "Nt-Methylhistidine content of mixed proteins in various rat tissues," Biochem. Biophys. Acta (1975) 405:67–71) showed that the mixed proteins in all of the organs sampled contained detectable levels of bound 3-methylhistidine. However, when examining each organ as a whole, it was found that skeletal muscle contained the majority (98%) of the total amount. This study did not include an assessment of the amount of 3-methylhistidine in skin and intestine. Intestinal tissue is also a source of 3-methylhistidine production in humans as measured in urine. Brenner, U. et al. (1987), "Der Einfluss des Dunndarms auf den 3-Methylhistidin-staffwechsel des Menschen (The effect of the small intestine on 3-methylhistidine metabolism in the human)", Infusionther. Klin. Ernahr. 14:248–251. Nishizawa et al. (Nishizawa, M. et al., "Fractional catabolic rates of myosin and actin estimated by urinary excretion of N-methyl histidine: the effect of dietary protein level on catabolic rates under conditions of restricted food intake," Br. J. Nutr. (1977) 37:345–353) concluded that the skin and intestine contributed up to 10% of the total body pool of 3-methylhistidine. Comparative turnover studies of 3-methylhistidine-containing proteins in intestine, skin and skeletal muscle suggest that the skin and the intestine contributed 17% of the 3-methylhistidine excreted per day in the urine (Millward, D. J. and P. C. Bates, "3-Methylhistidine turnover in the whole body, and the contribution of skeletal muscle and intestine to urinary 3-methylhistidine excretion in the adult rat," Biochem. J. (1983) 214:607–615). These calculated values are based on the fitting of exponential regression lines to the specific activity of 3-methylhistidine from the various tissues after giving a dose [methyl-$_3$H]methionine. The accuracy of this estimate is uncertain because the labeling technique used may be confounded by the reutilization of labeled methionine (Young, V. R. and H. N. Munro, "Nt-Methylhistidine (3-methylhistidine) and muscle protein turnover: an overview," Fed. Proc. (1978) 37:2291–2300). Millward et al. (Millward, D. J. et al., "Quantitative importance of non-skeletal-muscle sources of N-tau-methyl-histidine in urine," Biochem. J. (1980) 190:225–228) have also concluded that skeletal muscle, skin, and gastrointestinal tract contribute only 25, 7 and 10%, respectively, of the 3-methylhistidine excreted in the adult rat, with the remainder being excreted by some unknown organ. These values were based on a measurement of a decay curve of labeled 3-methylhistidine, after an injection of labeled methionine.

In contrast, following a duodenoileostomy in rats which left only 8% to 10% of small gut intact, it was concluded that the small intestine did not make a significant contribution to a 24-hour urinary excretion of 3-methylhistidine (Brenner, U. et al., "The contribution of small gut to the 3-methylhistidine metabolism in the adult rat," Metabolism (1987) 36:416–418). A similar study with short-bowel humans indicated that skeletal muscle was the major source of urinary 3-methylhistidine. In human patients with varying degrees of infection (Sjolin, J. et al., "Exchange of 3-methylhistidine in the splanchnic region in human infection," Am. J. Clin. Nutr. (1989) 50:1407–1414) it was concluded that urinary 3-methylhistidine was a valid marker of myofibrillar protein breakdown because it was correlated with the release of 3-methylhistidine from the leg. Furthermore, it was later shown with additional patients (Sjolin, J. et al., "Total and net muscle protein breakdown in infection determined by amino acid effluxes," Am. J. Physiol. (Endocrinol. Metab.) (1990) 258:E856–E863) that there was a significant linear relationship between the effluxes of tyrosine and phenylalanine and the efflux and urinary excretion of 3-methylhistidine.

A method to describe 3-methylhistidine metabolism in cattle has been described by using a compartmental model (Rathmacher, J. A. et al., "Technical Note: The use of a compartmental model to estimate the de novo production rate of Nt-methylhistidine in cattle," J. Anim. Sci. (1992) 70:2104–2108). The model showed similar results from plasma and urine. The model estimated 3-methylhistidine production. Fractional muscle breakdown was calculated from the production rate by assuming that muscle mass accounted for 33% of total mass of the steers. (Rathmacher, J. A. et al., "Technical Note: The use of a compartmental model to estimate the de novo production rate of Nt-methylhistidine in cattle," J. Anim. Sci. (1992)

70:2104–2108). Cattle quantitatively excrete 3-methylhistidine into the urine, as do humans (Harris, C. I. and Milne, G., "The urinary excretion of N-tau-methyl histidine by cattle: validation as an index of muscle protein breakdown," Br. J. Nutr. (1981) 45:411–422). 3-methylhistidine production can be described by the model.

A three-compartment mathematical model for analysis of plasma measurements of isotopic and natural 3-methylhistidine in lambs has been tested, resulting in the suggestion that pool (compartment) 3 may be a valid indicator of muscle mass in sheep. (Link, G. A. (1991), "A comprehensive approach to describing protein turnover in lambs," Ph.D. thesis, Department of Animal Science, Iowa State University.) However, sheep metabolize 3-methylhistidine differently than humans, i.e., not all of it is excreted in the urine but, as discussed above, part is converted to balenine and stored in the muscles.

A similar kinetic approach can be utilized in sheep and swine (Rathmacher, J. A. et al., "Measurement of 3-methylhistidine production in lambs by using compartmental-kinetic analysis," Br. J. Nutr. (1992) 69:743–755; Rathmacher, J.A. et al., "Estimation of 3-methylhistidine production in swine by compartmental analysis," J. Anim. Sci. (1992) Abstract, 70:194) which, unlike humans, retain 3-methylhistidine in muscle as the dipeptide balenine (Harris, C. I. and Milne, G., "The urinary excretion of Nt-methyl histidine in sheep: an invalid index of muscle protein breakdown," Br. J. Nutr. (1980) 44:129–140; Harris, C. I. and Milne, G., "The inadequacy of urinary (N-tau)-methyl histidine excretion in the pig as a measure of muscle protein breakdown," Br. J. Nutr. (1981) 45:423–429).

Muscle is degraded in response to many metabolic situations including: starvation, infection, surgery, diabetes, nutrition level, hormonal and stress conditions. Scientific advances in these clinical areas are limited due to limitations in methodology available to quantitate myofibrillar proteolysis versus proteolysis of muscle as a whole. The protein reserve of skeletal muscle is composed of two distinct fractions; myofibrillar protein, the structural component, and non-myofibrillar, non-structural component. The myofibrillar protein makes up 60% of the skeletal muscle protein and turnover slower than non-myofibrillar protein (Bates, P. C. et al., "Myofibrillar protein turnover: synthesis of protein-bound 3-methylhistidine, actin, myosin heavy chain and aldolase in rat skeletal muscle in the fed and starved states," Biochem. J. (1983) 214:593–605). There is also evidence to show that myofibrillar and non-myofibrillar are not under the same metabolic control nor degraded by the same mechanism (Lowell, B. B. et al., "Regulation of myofibrillar protein degradation in rat skeletal muscle during brief and prolonged starvation," Metabolism (1986) 35:1121–1127; Lowell, B. B. et al., "Evidence that lysosomes are not involved in the degradation of myofibrillar proteins in rat skeletal muscle," Biochem. J. (1986) 234:237–240; Goodman, M. N., "Differential effects of acute changes in cell Ca2+ concentration on myofibrillar and non-myofibrillar protein breakdown in the rat extensor digitorum longus muscle in vitro: Assessment by production of tyrosine and N-tau-methylhistidine," Biochem. J. (1987) 241:121–127).

An insignificant increase in 3-methylhistidine excretion in humans during exercise and a significant increase during recovery from exercise has been reported, suggesting that exercise does not result in significant depletion of muscle mass. Carraro, F. (1990), "Effect of exercise and recovery on muscle protein synthesis in human subjects," Am. J. Physiol. 259E470–476.

As an alternative to measuring urinary 3-methylhistidine, the difference between plasma 3-methylhistidine measurements of venous and arterial flows in humans has been used to determine 3-methylhistidine afflux in patients with myotonic dystrophy; this difference was found not to correlate with the presence of myotonic dystrophy, suggesting that myofibrillar protein degradation is not increased in myotonic dystrophy.

All publications referred to herein are incorporated in their entirety by reference.

There is thus a need in the art for the measurement of muscle mass in humans which has greater accuracy and is subject to less interference by extraneous factors than prior art tests.

BRIEF DESCRIPTION OF THE DRAWINGS

FIG. 4A shows the model useful for cattle and humans. FIG. 4B shows the sheep model and FIG. 4C shows the swine model.

SUMMARY OF THE INVENTION

Figure 1:
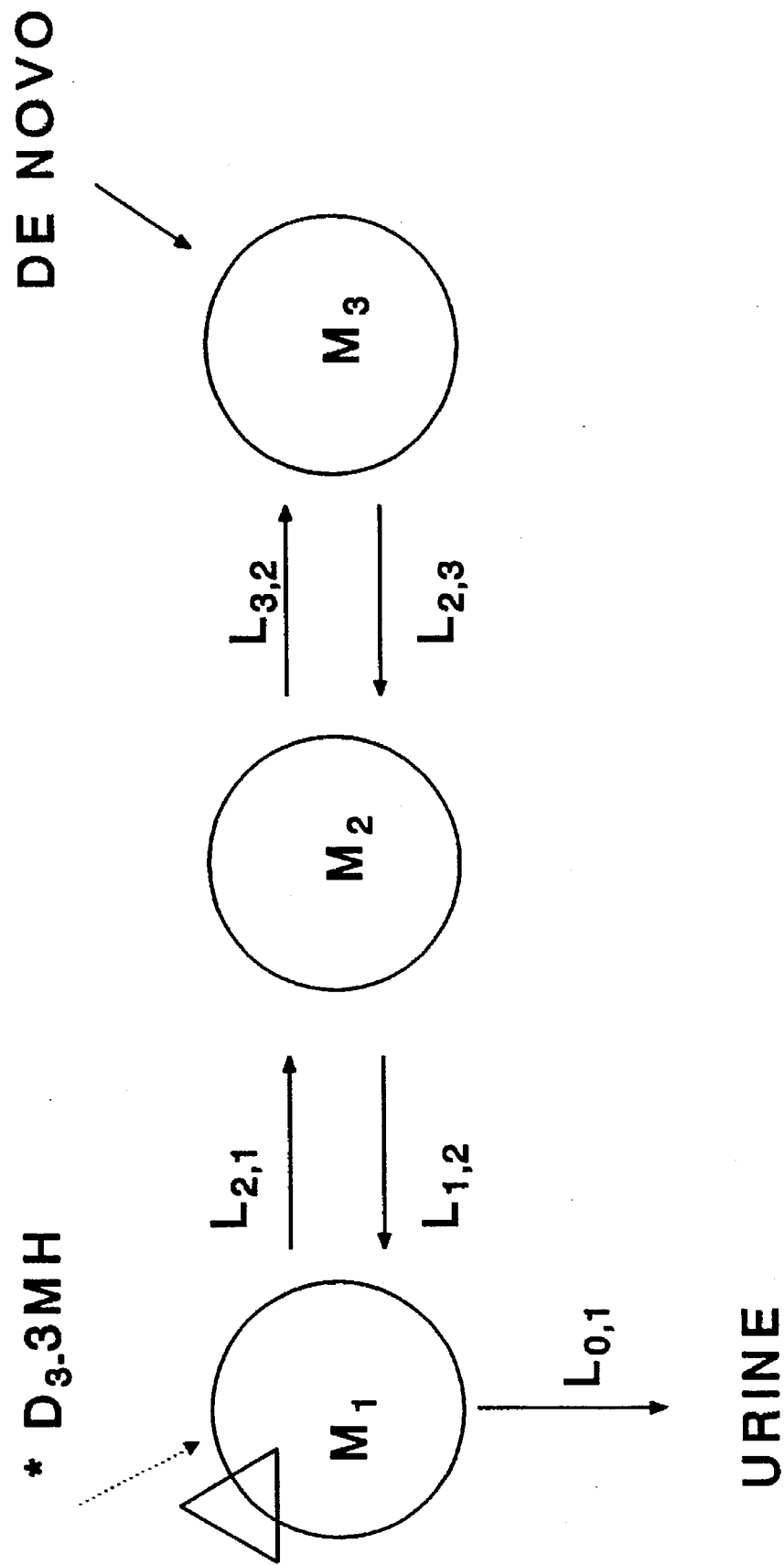
FIG. 1. Schematic of a 3-compartment model used to analyze the kinetics of distribution, metabolism, and de novo production of 3-methylhistidine (3-methylhistidine). $M_1$, $M_2$, and $M_3$ represent the mass of 3-methylhistidine in compartments 1, 2 and 3, respectively. $L_{2,1}$, $L_{1,2}$, $L_{0,1}$, $L_{3,2}$, and $L_{2,3}$ are fractional transfer rate coefficients of 3-methylhistidine within the system. The tracer, 3-[$^2H_3$-methyl]-methylhistidine ($D_3$-3-methylhistidine), was injected into compartment 1. Sampling was performed from compartment 1. De novo production of 3-methylhistidine was into compartment 3.

A method for determining muscle mass in a human subject is provided. The method may be used for monitoring athletic conditioning, weight loss programs, nutritional deficiencies, and disease states which cause muscle wasting such as muscular dystrophy. The method involves administration of a bolus dose of a metabolic marker (also called "tracer" herein) for 3-methylhistidine and the use of a three-compartment kinetic model to describe data collected from blood samples collected periodically thereafter.

An important advantage of the compartmental model is that it provides additional information about the metabolism and distribution of 3-methylhistidine which urinary 3-methylhistidine measurements cannot provide. This method does not necessitate quantitative urine collection; reduces error due to the frequency of plasma sampling vs. the infrequency of urine collection; and in providing detailed information about compartment size and transfer rates, allows more accurate and efficient determinations of muscle mass than previously-known methods.

The method of this invention for measuring muscle mass in a human subject comprises:

(a) obtaining the total body weight of the subject;

(b) administering to said subject a known amount of a metabolic marker for 3-methylhistidine;

(c) periodically removing blood or urine samples from said subject and recording the time to the nearest second;

(d) measuring the amount of said marker and of 3-methylhistidine in each such sample;

(e) generating a three-compartment mathematical model from said measurements comprising values for the functional transfer rates in and out of said compartments, values for the mass of 3-methylhistidine in each compartment and values for the mass transfer rates of 3-methylhistidine in and out of said compartments;

(f) calculating muscle mass as a function of the numerical value of at least one of said values and the total body weight of the subject.

As used herein, $M_1$, $M_2$ AND $M_3$ are mass of 3-methylhistidine in nmol; $R_{ij}$ is the mass transfer rate in nmol/min; and $L_{ij}$ is the fraction/min transferred.

Metabolic markers for 3-methylhistidine may be any markers known to the art including radioactive isotopes of 3-methylhistidine such as $^{14}C$-labelled 3-methylhistidine, and stable, non-radioactive isotopes of 3-methylhistidine such as 3-[$^2H_3$-methyl]-methylhistidine ($D_3$-3-methylhistidine) and 3-[$_{13}C$]methylhistidine. $D_3$-3-methylhistidine is a preferred marker of this invention.

Administration may be oral or intravenous, and is preferably intravenous. Any site may be used for administration of the marker, as is known to the art.

The amount of marker administered should be between about 0.2 nmol/kg and about 0.8 nmol/kg body weight, preferably between about 0.2 and about 0.6, and most preferably between about 0.2 and about 0.3. When administered orally, the does is usually at the higher end of the range. $D_3$-3-methylhistidine administered in such small quantities is non-toxic and is quantitatively excreted in urine.

Blood or urine samples are periodically taken from the patient, as is known to the art, preferably in an amount of between about 2.5 and about 10 mL per sample. Samples are preferably taken over a period sufficient to achieve steady state decay. Generally, samples should be taken over a period of at least about 48 hours, preferably between about 48 and about 72 hours, and more preferably about 60 hours.

At least about 12 blood or urine samples should be taken over this period, preferably evenly spaced over the period. More preferably between about 10 and about 18 samples are taken, and most preferably about 14 samples are taken.

The amount of marker and 3-methylhistidine in each sample is measured by any means known to the art, preferably by gas chromatography mass spectroscopy utilizing 1,1-($^{18}O_2$)1-methylhistidine as an internal standard (meat diet) or 1-methylhistidine as an internal standard (meat-free diet).

A three-compartment mathematical model is then generated from these measurements, preferably using a Simulation, Analysis and Modeling (SAAM) computer program as more fully described hereinafter. The three-compartment mathematical model of this invention is depicted in FIG. 1. Applicants have discovered that the three-compartment model most accurately and simply describes the system and provides data for accurate measurement of muscle mass. A two-compartment model was found to be inadequate, while little or no gain in accuracy was obtained using a four-compartment model. While the compartments are not literally described as corresponding to particular locations in the body, applicants have determined that compartment 1 ($M_1$) may be roughly thought of as corresponding to the plasma and extracellular space and compartments 2 ($M_2$) and 3 ($M_3$) may be roughly thought of as corresponding to intracellular space (within the muscles).

Muscle mass may be calculated using values generated from using the three-compartment model. Muscle mass may be calculated using total body weight and the mass of 3-methylhistidine in compartment 2 by the equation:

$$\text{Muscle (kg)} = -31.96 + 0.0000027(M_2) + 0.80 \text{ (wt)}$$

where $M_2$ is the mass of 3-methylhistidine in compartment 2, and wt is body weight (kg).

Alternatively, muscle mass may be calculated using the fractional transfer rate of 3-methylhistidine from compartment 1 into urine and the mass of 3-methylhistidine in compartment 2 using the equation:

$$\text{Muscle (kg)} = -9.90 + 3039.5(L_{0,1}) + 0.000155(M_2)$$

where $L_{0,1}$ is the fractional transfer rate (min$^{-1}$) for 3-methylhistidine from compartment 1 ($M_1$) into urine (0), and $M_2$ is the mass of 3-methylhistidine in compartment 2 (nmol).

Additional accuracy is possible when body weight is also used to calculate muscle mass. The following equation is used:

$$\text{Muscle mass (kg)} = -32.39 - 0.00035(M_2) - 783.194(L_{0,1}) + 0.927 \text{ (wt)}$$

where wt is body weight (kg).

Additional accuracy is possible when the mass transfer rate of 3-methylhistidine from compartment 2 into compartment 1 ($R_{1,2}$) is used. The following equation is used:

$$\text{Muscle mass (kg)} = -40.16 - 0.000031(M_2) - 1000.69(L_{0,1}) - 0.0021(R_{1,2}) + 1.15 \text{ (wt)}$$

where $R_{1,2}$ is the mass transfer rate from compartment 2 to compartment 1 (nmol·min$^{-1}$).

Alternatively, muscle mass is calculated as a function of the following values: $L_{1,2}$, $L_{0,1}$, $M_1$, $R_{2,3}$ and wt using the equation:

$$\text{Muscle mass (kg)} = -22.02 - 255.13(L_{1,2}) - 2498.4(L_{0,1}) - 0.000579(M_1) + 0.00486(R_{2,3}) + 1.27 \text{ (wt)}$$

where $L_{1,2}$ is the fractional transfer rate of 3-methylhistidine from compartment 2 to compartment 1 (min$^{-1}$), $L_{0,1}$ is the fractional transfer rate of 3-methylhistidine from compartment 1 into urine (0) (min$^{-1}$), $M_1$ is the mass of 3-methylhistidine in compartment 1 (nmol), and $R_{2,3}$ is the mass transfer rate of 3-methylhistidine from compartment 3 to compartment 2 (nmol·min$^{-1}$).

Prior to testing, the subject is preferably placed on a meat-free diet for at least about 72 hours. Alternatively, the subject may be asked to fast for at least about 12 hours prior to the test. Preferably, meat is excluded from the diet for at least about three days and the subject is asked to fast overnight prior to the test.

DETAILED DESCRIPTION OF THE PREFERRED EMBODIMENTS

A preferred method of measuring muscle mass provided herein involves administration of a bolus dose of $D_3$-3-methylhistidine of about 0.20 µm/kg administered intravenously into the forearm vein of the dominant arm. Blood samples are taken at regular intervals over a twelve hour period, more frequently during the first 90 minutes, e.g. at 0, 2, 5, 10, 15, 30, 45, and 90 minutes, followed by further samples at 150, 210, 270, 330, 720, 1440, 2160, 2880 and 3600 minutes.

The concentrations of 3-methylhistidine and $D_3$-3-methylhistidine are measured by gas chromatography mass spectroscopy in each sample, and the ratio of isotopic to natural 3-methylhistidine in each sample entered into a SAAM modeling program on personal computer to generate a three-compartment model. The three-compartment model provides values for the mass of 3-methylhistidine in each compartment and for the mass transfer rates of 3-methylhistidine in and out of each compartment.

The values are then used to calculate muscle mass for each subject.

EXAMPLE 1

Determination of Fat Free Mass as a Function of $M_2$.

Normal volunteers with no evidence or history of diabetes mellitus or of cardiac, liver, renal or pulmonary diseases were studied. The subjects consisted of 3 males and 1 female, ranging in age from 31 to 37 years, in body weight from 47 to 92 kg, and in body mass index (BMI) from 19.2 to 25.5. The purpose and possible risks of the study were explained to all subjects, and their voluntary written consent was obtained. The study protocol was approved by the Committee for the Protection of Human Subjects of the Institutional Review Board at Vanderbilt University School of Medicine. All studies were performed at the Clinical Research Center (CRC). Subjects were placed on balanced weight-maintenance diets for at least one week before the start of the study. Meat was excluded from the subjects' diets for three days before the study and during the study.

All studies were performed after a 10–12 hour overnight fast. On the morning of the experiment (6.30 to 7.00 hours), an 18-gauge Angiocatheter™ (Benton Dickinson, Sandy, Utah) was placed in a superficial hand vein of the nondominant arm for blood sampling. The hand was heated to 55° C. to ensure complete arterialization (Abumrad, N.N. et al., "Use of a heated superficial hand vein as an alternative site for the measurement of amino acid concentrations and for the study of glucose and alanine kinetics in man," Metabolism (1981) 30:936–940). In addition, a 16-gauge angiocatheter was inserted into the contralateral forearm vein for the infusion of L-3-[methyl-$^2H_3$]-histidine (MSD Isotopes, Montreal, Canada). Finally, another catheter was threaded retrograde into the brachial vein of the dominant arm and used for sampling of the forearm tissue.

Each study was four days in duration. Starting at t=0 (8.00 hours), subjects were administered a bolus infusion of L-3-[methyl$^2H_3$]-histidine ($D_3$-3-methylhistidine) at 0.13 µmol/kg into the forearm vein of the dominant arm. The infusate was passed through a Millex-GS sterilizing filter (0.22 µm; Millipore Products Divisions, Bedford, Mass.) before the infusion. Blood samples were obtained from the superficial hand vein and from the deep forearm vein at 0, 1, 2, 5, 10, 15, 30, 45, 90, 150, 210, 270, 330, and 720 min. postinjection. During this time, the subjects were required to stay at the Clinical Research Center, although they were allowed to ambulate freely within their rooms. Free access to food and drink was allowed after the 330-min sample. After 720 min, the catheters were removed and the patients were allowed to go home. For the following three days, the subjects returned to the CRC each morning before eating for further blood sampling by percutaneous venous puncture at 1,440, 2,880, and 4,320 min postinjection. Urine was collected over 24 hour periods the day before and for three days after tracer infusion.

Blood was collected in heparinized syringes, transferred to tubes containing Na$_2$EDTA (15 mg/tube), and centrifuged. The plasma obtained was immediately placed on ice. An aliquot of the plasma was processed for determination of 3-methylhistidine concentration as well as the L-3-[methyl-$^2H_3$]-histidine:3-methylhistidine isotope enrichment. The remainder of the plasma was frozen at −70° C. The urine obtained was processed for the determination of creatinine both as a measure of the completeness of the collection (Pencharz, P. B. et al., "The effect of an energy-restricted diet on the protein metabolism of obese adolescents: nitrogen-balance and whole-body nitrogen turnover," Clin. Sci. (1980) 59:13–18), and for the estimation of lean body mass (Blackburn, G. L. et al., "Nutritional and metabolic assessment of hospitalized patients," J. Parenter. Enteral. Nutr. (1977) 1:11–22). Urinary 3-methylhistidine concentration and production were also measured (Rathmacher, J. A. et al., "Gas chromatographic-mass spectrometric analysis of stable isotopes of 3-methylhistidine in biological fluids: application to plasma kinetics in vivo," Biol. Mass Spectrom. (1992) 21:560–566).

Body composition was determined for each subject from the measurements of body density estimated by underwater weighing (Goldman, R. F. and Buskirk, E. R., "Body volume measurement by underwater weighing: description of a method," In: *Techniques for measuring body composition*, J. Brozek (ed) Washington D.C., National Academy of Sciences (1961) 78–79). Body weights in air and underwater were measured to the nearest 25 g by using Detecto (Webb City, Mo.) and Chatilion Spring (New Gardens, N.Y.) scales, respectively. Residual lung volume was determined (simultaneously with underwater weighing) with a closed-circuit, nitrogen-dilution method (Pencharz, P.B. et al., "The effect of an energy-restricted diet on the protein metabolism of obese adolescents: nitrogen-balance and whole-body nitrogen turnover," Clin. Sci. (1980) 59:13–18). Nitrogen concentration during rebreathing was measured with a Med-Science 505-D Nitralizer (St. Louis, Mo.). The percentage of body fat was estimated from body density by using the revised equation of Lohman et al. (Lohman, T. G. et al., "Bone and mineral measurements and their relation to body density in children, youth and adults," Hum. Biol. (1984) 56:667–679).

The enrichment of $D_3$-3-methylhistidine was quantitated in blood over time. The baseline enrichment was subtracted from experimental samples. $D_3$-3-methylhistidine decay from plasma was evaluated using a compartmental model developed through the use of the Simulation, Analysis and Modeling program (SAAM/CONSAM-31.0β) (Berman, M. and Weiss, M. F., SAAM Manual, US Department of HEW Publication No. (NIH) 78–180. US GPO, Washington, D.C. (1978), incorporated herein by reference; Boston, R. C. et al., "Conversational SAAM—an inter-reactive program for kinetic analysis of biological systems," Comp. Prog. Biomed (1981) 13:111, incorporated herein by reference) on a personal computer. The model, illustrated in FIG. 1, was configured by entering the isotope ratio in plasma of the $D_3$-3-methylhistidine:natural 3-methylhistidine into compartment 1 over time as described for models using stable isotope kinetic data (Cobelli, et al., "Models to interpret kinetic data in stable isotope tracer studies," Am. J. Physiol. (Endocrinol. Metab.) (1987) 253:E551–E564). The ratio was standardized by dividing the isotope ratio by the dose of tracer in the bolus injection. The model was solved using SAAM and allowed to converge on the observed tracer data, and produced transfer coefficients that minimized the weighted total sum of squares between observed and calculated data points. Model code 10, which uses a set of linear differential equations having constant coefficients, was used to explain the tracer data. A minimum of three compartments were needed to accurately describe the kinetics and metabolism of 3-methylhistidine. The model consisted of three compartments or pools of 3-methylhistidine; the only exit from model was out of pool 1. A steady-state solution was also obtained and initialized by setting the mass of compartment 1 equal to the mean concentration of natural 3-methylhistidine in the plasma multiplied by the space of distribution in compartment 1. Compartmental masses and flux of 3-methylhistidine between compartments were also acquired.

In this model, compartment 1 is assumed to represent plasma and extracellular fluid, while compartments 2 and 3 are probably tissue pools of intracellular 3-methylhistidine. The predicted irreversible loss into urine from compartment 1 was derived from the de novo production of 3-methylhistidine as it appears into an intracellular tissue compartment 3.

Steady state masses and transport rates were calculated, and the de novo production rate was calculated and used to calculate a fractional degradation rate for the myofibrillar proteins. Steady state calculations were initialized by multiplying plasma 3-methylhistidine concentration (nmol/mL) by the initial space of compartment 1. The initial space of distribution is calculated experimentally from the kinetic data as a proportionality constant. The remainder of compartment masses and fluxes of 3-methylhistidine were resolved form the three differential equations that describe the model. No meat was fed to the subjects, so the only source of 3-methylhistidine entering the model was from de novo production which is depicted in the model as an arrow into compartment 3. Models were evaluated by performing an F test on the sum of squares for each model (Jones, R.H. et al., "Statistical identification of compartmental models with application to plasma protein kinetics," Comp. Biomed. Res. (1984) 17:277–288). Individual model parameters were evaluated by the coefficient of variation. A coefficient of variation of less than 50% was determined adequate for each parameter.

Values are presented for each individual subject as well as mean ±SE. Means for 3-methylhistidine production and for 3-methylhistidine to creatinine ratio for model- and urine-based calculations were compared by a t-test (Steele, R.G.D. and Torrie, J. H., *Principles and Procedures of Statistics: A Biometrical Approach*, New York: McGraw-Hill Book Co., 1980). Pearson correlation coefficients were used to evaluate the relationship between model parameters and body composition using the SAS statistical software (SAS Inst., Inc., Cary, N.C.).

Table 1 presents measurements of body composition, including estimates of fat (kg), body mass index, $kg/m^2$ (BMI), % fat, and fat free mass (FFM, kg) for each individual subject. Lean body mass was correlated to compartments of the model (Table 3). The compartment 2 mass ($M_2$, nmoles) was positively correlated with FFM (P=0.9), and the model estimate of 3-methylhistidine production was correlated with FFM but not significantly (r=0.74, P=0.25), whereas urinary creatinine was not correlated with FFM (r=0.36, P=0.64). BMI and fat were positively correlated with $M_3$ (P=0.16 and P=0.08).

Figure 2:
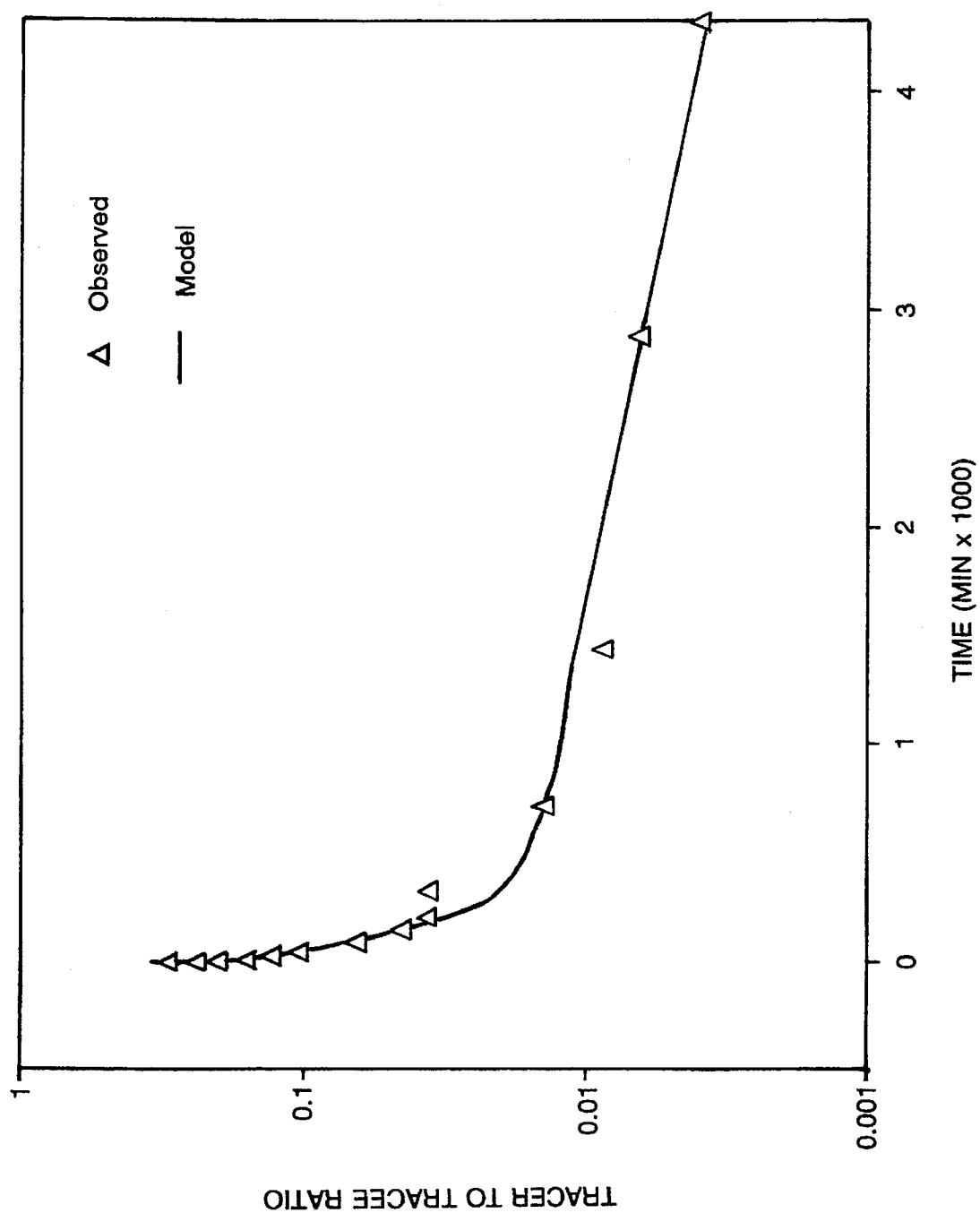
FIG. 2. Disappearance of tracer, 3-[$^2H_3$-methyl]-methylhistidine, as a ratio of 3-[$^2H_3$-methyl]-methylhistidine:3-methylhistidine in plasma as described by the 3-compartment model of 3-methylhistidine. Symbols (▲) represent observed data, and the line (-) represents best fit generated by the model.

Plasma levels of 3-methylhistidine did not change over the four days of the study, so steady state was assumed. A representative decay of $D_3$-3-methylhistidine:3-methylhistidine is presented in FIG. 2. The decay curve is characterized by a rapid decrease in the $D_3$-3-methylhistidine:3-methylhistidine ratio during the first 5 hours followed by a slow linear (semilog plot) decay over the three days of blood sampling.

The kinetic model parameters ($L_{ij}$) are presented in Table 2. Variations of the parameters were evaluated by the coefficient of variation (%CV=100×SD÷mean) of each individual parameter. Ranges for %CV were from 16 to 43% for $L_{2,1}$, 24 to 46% for $L_{1,2}$, 9 to 136% for $L_{0,1}$, 12 to 49% for $L_{3,2}$, and 15 to 115% for $L_{2,3}$. These parameters were within the acceptable range, except for $L_{0,1}$ and $L_{2,3}$ of subject A which were above 100%. A %CV greater than 100% is not acceptable for a model parameter estimation (Wolfe, Robert R., *Radioactive and Stable Isotopes Tracer in Biomedicine: Principles and Practice of Kinetic Analysis*, New York: Wiley-Liss (1992) 145–165). In previous studies using cattle, the %CV's for the $L_{ij}$ were less than 50%. The larger %CV for parameters $L_{0,1}$ and $L_{2,3}$, particularly for subject A, may be explained by too few points between 300 and 1440 min; additional data points will be needed to lower the variation. The 3-methylhistidine model compartment mass ($M_i$) and mass transfer rates ($R_{ij}$) are presented in Table 2. Compartment 2 is 1.5 times larger than compartment 1, and compartment 3 is 13 times larger than compartment 1.

Figure 3A:
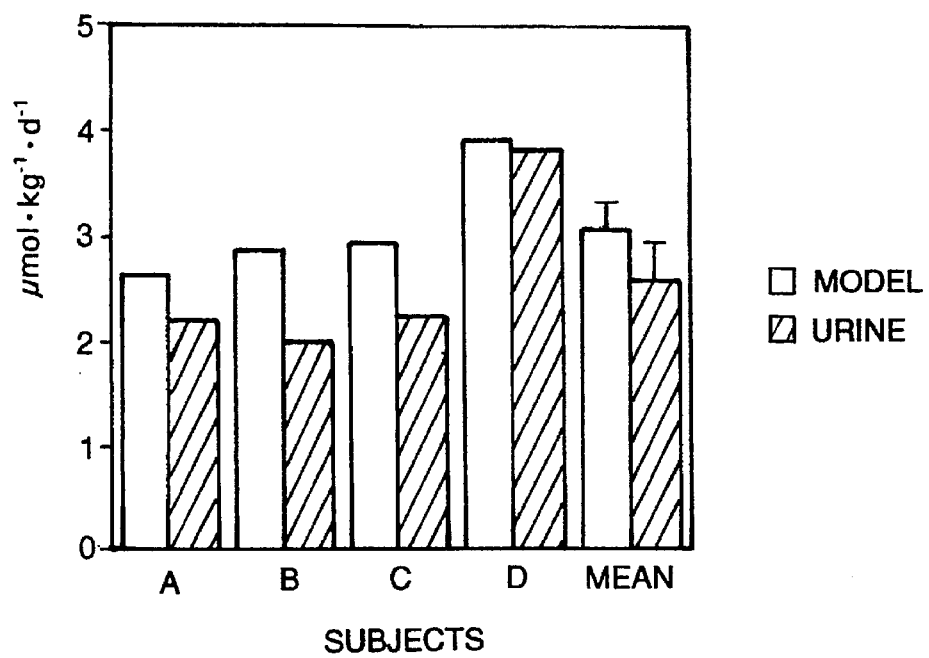
FIG. 3A: Daily 3-methylhistidine production expressed as $\mu mol \cdot kg^{-1} \cdot d^{-1}$ for each individual subject and a mean of four individuals as calculated from urinary excretion (hatched bars) and by a 3-compartment model of 3-methylhistidine production (solid bars). There was no mean difference between urinary and model 3-methylhistidine production, P>0.30.
Figure 3B:
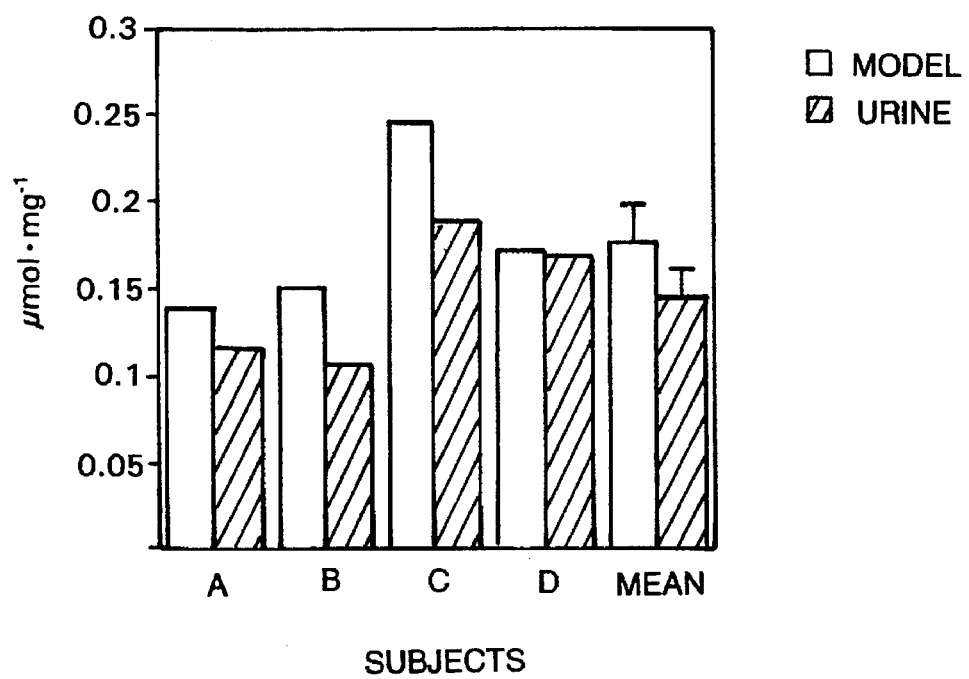
FIG. 3B: Daily 3-methylhistidine:creatinine ratio, $\mu mol \cdot mg^{-1}$ for each individual subject and a mean of the four individuals as calculated from urinary excretion (hatched bars) and by a 3-compartment model of 3-methylhistidine production (solid bars). There was no mean difference between urinary and model 3-methylhistidine:creatinine ratio, P>0.30.

The calculated de novo production rate of 3-methylhistidine and the urinary 3-methylhistidine excretion is presented in FIG. 3 expressed as $\mu mol \cdot kg^{-1} \cdot d^{-1}$, and they were also expressed as a 3-methylhistidine:creatinine ratio ($\mu mol \cdot mg^{-1}$). In both cases the model estimate of 3-methylhistidine production was not different (P>0.30) from urinary 3-methylhistidine production. Urinary 3-methylhistidine production was lower than the model estimate of 3-methylhistidine production in each subject, but these variables were highly correlated (r=0.97, P=0.033).

Table 3 presents the relationship of model parameters to urinary 3-methylhistidine and body composition and shows $M_2$ to be highly correlated to fat free mass.

An objective of the present study was to determine whether a de novo production rate of 3-methylhistidine as estimated by the isotope model was similar to urinary 3-methylhistidine production. The slope of curve (FIG. 2) was similar to that of other species evaluated with this model (Rathmacher, J. A. et al. (1992), "Technical Note: the use of a compartmental model to estimate the de novo production rate of N-methylhistidine in cattle," J. Anim. Sci.

70:2104–2108; Rathmacher, J. A. et al. (1993), "Measurement of 3-methylhistidine production in lambs by using compartmental-kinetic analysis," Brit. J. Nutrition 69:743–755; Rathmacher, J. A. et al., "Estimation of 3-methylhistidine production in swine by compartmental analysis," J. Anim. Sci. (1992) 70:194 (Abstract)). The in vivo kinetics of 3-methylhistidine in human subjects can be described by means of a simple serial model of 3-compartments and sampling of only plasma. The kinetic parameters, $L_{ij}$, compartment mass $M_i$ and mass transfer rates $R_{ij}$ are presented as a reference for future modeling of 3-methylhistidine metabolism.

The $L_{ij}$ parameters for human subjects were similar to those reported for cattle except for $L_{2,1}$ which was lower for humans (0.18 in cattle versus 0.07 $min^{-1}$ in humans). Table 5 provides a summary of three studies: Rathmacher, J. A. et al., "Evaluation of muscle protein turnover in steers differing in mature size (1993), unpublished; Rathmacher, J. et al., "The use of compartmental models of 3-methylhistidine flux to evaluate skeletal muscle protein turnover in implanted steers," J. Anim. Sci. (1993) 71:135 (Abstract); and Rathmacher, J. A. et al., "Technical Note: The use of a compartmental model to estimate the de novo production rate of Nt-methylhistidine in cattle," J. Anim. Sci. (1992) 70:2104–2108. Based on the size of compartment 1, $M_1$ has a mass similar to extracellular water space and $M_2$ and $M_3$ are most consistent with intracellular pools of 3-methylhistidine (Table 2). Muscle biopsy data from lambs (Rathmacher, J. A. et al. (1993), "Measurement of 3-methylhistidine production in lambs by using compartmental-kinetic analysis," Brit. J. Nutrition 69:743–755) indicate that compartments 2 and 3 appear to be muscle specific for 3-methylhistidine in muscle.

The present study confirmed that model estimates of 3-methylhistidine production correspond to urinary 3-methylhistidine production. Means were not different when expressed on body weight basis or on urinary creatinine basis, but they were 16% higher than urinary estimates. Similar correlations were measured in cattle (Rathmacher, J. A. et al. (1992), "Technical Note: the use of a compartmental model to estimate the de novo production rate of N-methylhistidine in cattle," J. Anim. Sci. 70:2104–2108) where model and urinary 3-methylhistidine production results were similar but tended to be higher than urine values. This could be due to minor losses in urine or small amounts of 3-methylhistidine metabolism/conjugation in humans.

TABLE 1

Subject characteristics

| Parameter | Subjects | | | |
|---|---|---|---|---|
| | A | B | C | D |
| Age, years | 35 | 37 | 31 | 31 |
| Sex | ♂ | ♀ | ♂ | ♂ |
| Weight, kg | 92 | 47 | 78 | 69 |
| Body Mass Index, kg/m²* | 25.5 | 19.2 | 21.6 | 24.4 |
| Fat, %* | 32.3 | 28.7 | 13.5 | 22.4 |
| Fat, kg* | 29.1 | 13.7 | 10.0 | 18.13 |
| Fat-free mass, kg* | 61.1 | 34.0 | 64.3 | 50.8 |

*Body composition was determined for each subject from the measurements of body density estimated by underwater weighing (Goldman, R. F. and Buskirk, E. R., "Body volume measurement by underwater weighing: description of a method," In: Techniques for Measuring Body Composition (Brozek, J. ed.) Washington, D.C.: Nat'l Acad. of Sciences (1961) p. 78–79). The percentage of body fat was estimated from body density by using the revised equation of Lohman et al. (Lohman, T. G. et al., "Bone and mineral measurements and their relation to body density in children, youth and adults," Hum. Biol. (1984) 56:667–679).

TABLE 2

Kinetic parameters of 3-methylhistidine metabolism and 3-methylhistidine model masses and mass transfer rates.*

| Parameter | Subjects | | | | | |
|---|---|---|---|---|---|---|
| | A | B | C | D | Mean | SE† |
| $L_{2,1}$, $min^{-1}$‡ | 0.0509 | 0.1573 | 0.0196 | 0.1372 | 0.0759 | 0.0686 |
| $L_{1,2}$, $min^{-1}$ | 0.0224 | 0.1505 | 0.0111 | 0.1887 | 0.0614 | 0.0944 |
| $L_{0,1}$, $min^{-1}$ | 0.0048 | 0.0051 | 0.0024 | 0.0035 | 0.0041 | 0.0017 |
| $L_{3,2}$, $min^{-1}$ | 0.0051 | 0.0141 | 0.0074 | 0.0148 | 0.0089 | 0.0074 |
| $L_{2,3}$, $min^{-1}$ | 0.0004 | 0.0017 | 0.0029 | 0.0016 | 0.0017 | 0.0008 |
| $M_1$, nmol · $kg^{-1}$§ | 383 | 390 | 858 | 780 | 603 | 109 |
| $M_2$, nmol · $kg^{-1}$ | 952 | 421 | 1692 | 581 | 912 | 245 |
| $M_3$, nmol · $kg^{-1}$ | 15856 | 3584 | 5070 | 7240 | 7938 | 2377 |
| $U_3$, nmol · $kg^{-1}$ · $min^{-1}$** | 1.83 | 2.00 | 2.04 | 2.72 | 2.15 | 0.17 |
| $R_{2,1}$, nmol · $kg^{-1}$ · $min^{-1}$†† | 19.49 | 61.36 | 16.83 | 106.94 | 51.15 | 18.37 |
| $R_{1,2}$, nmol · $kg^{-1}$ · $min^{-1}$ | 21.31 | 63.35 | 18.87 | 109.66 | 53.30 | 18.52 |
| $R_{0,1}$, nmol · $kg^{-1}$ · $min^{-1}$ | 1.83 | 2.00 | 2.04 | 2.72 | 2.15 | 0.17 |
| $R_{3,2}$, nmol · $kg^{-1}$ · $min^{-1}$ | 4.86 | 5.95 | 12.50 | 8.62 | 7.98 | 1.47 |
| $R_{2,3}$ nmol · $kg^{-1}$ · $min^{-1}$ | 6.69 | 5.95 | 14.55 | 11.34 | 19.63 | 1.75 |

*The kinetic parameters for a 3-compartment model of 3-methylhistidine metabolism are presented for each subject along with the mean and †standard error. ‡$L_{i,j}$, fractional transfer from compartment i to compartment j. §$M_i$, mass of compartment i; **$U_3$, de novo production into compartment 3; ††$R_{ij}$, mass transfer rate from compartment j to compartment i.

TABLE 3

Relationship of model parameters to urinary
3-methylhistidine production and body composition*.

| Correlation | Coefficient | P-value |
|---|---|---|
| 3-Methylhistidine production model to urine† | 0.97 | 0.03 |
| Body composition to model parameters | | |
| fat free mass to $M_2$‡ | 0.91 | 0.09 |
| fat free mass to model 3MH§ | 0.74 | 0.26 |
| fat mass to $M_3$ | 0.92 | 0.08 |
| body mass index to $M_3$ | 0.84 | 0.16 |

*Model is a 3-compartment model of 3-methylhistidine production. †3-Methylhistidine production for model and urine have the units μmol · $d^{-1}$. ‡Fat free mass has the units of kg, and $M_2$ is mass of compartment 2 in nmoles. §Model 3-methylhistidine is the estimate of production expressed as μmol · $d^{-1}$. **Fat mass has the units of kg, and $M_3$ is the mass of compartment 3 in nmoles.

EXAMPLE 2

Comparison of Human and Animal 3-methylhistidine Models.

The differences between 3-methylhistidine metabolism in humans as found in Example 1 and other animals is shown in Table 5. For cattle, the same three-compartment model was used as described herein. With respect to sheep, the model differs from that shown in FIG. 1 in that de novo production of 3-methylhistidine is shown in compartment 2 and additionally, exit from compartment 3 occurs as well as from compartment 1 into urine. With respect to swine, again, de novo production of 3-methylhistidine is shown in compartment 2, and exit to urine is from compartment 3.

TABLE 4

Summary of 3-methylhistidine metabolism
as described by a 3-compartment model.
Included are mass of compartments and mass transfer rates.

| Parameter | Human | Cattle* | Pigs† | Sheep§ | Dogs¶ |
|---|---|---|---|---|---|
| n | 4 | 36 | 20 | 36 | 5 |
| $M_1$, nmol · $kg^{-1}$** | 603 | 806 | 1110 | 4693 | 3227 |
| $M_2$, nmol · $kg^{-1}$ | 912 | 2106 | 2857 | 11634 | 7973 |
| $M_3$, nmol · $kg^{-1}$ | 7938 | 7803 | 6151 | 16494 | 9261 |
| $R_{21}$, nmol · $kg^{-1}$ · $min^{-1}$ | 51 | 103 | 247 | 928 | 319 |
| $R_{12}$, nmol · $kg^{-1}$ · $min^{-1}$ | 53 | 107 | 247 | 930 | 329 |
| $R_{32}$, nmol · $kg^{-1}$ · $min^{-1}$ | 7.9 | 5.4 | 37 | 84 | 56 |
| $R_{23}$, nmol · $kg^{-1}$ · $min^{-1}$ | 9.6 | 9.6 | 32 | 80 | 56 |
| $R_{01}$, nmol · $kg^{-1}$ · $min^{-1}$ | 2.2 | 4.2 | NA | 1.4 | 9 |
| $R_{03}$, nmol · $kg^{-1}$ · $min^{-1}$ | NA | NA | 5.0 | 5.7 | NA |
| 3MH Production, μmol · $kg^{-1}$ · $d^{-1}$ | 3.1 | 6.2 | 7.2 | 10.1 | 12 |

*Data obtained from cattle experiments (reported in Rathmacher, J. A. et al. (1992), "Technical Note: the use of a compartmental model to estimate the de novo production rate of N-methylhistidine in cattle," J. Anim. sci. 70:2104–2108; Rathmacher, J. et al., "The use of compartmental models of 3-methylhistidine flux to evaluate skeletal muscle protein turnover in implanted steers," J. Anim. Sci. (1993) 71:135 (Abstract); Rathmacher, J. A. et al., "Evaluation of muscle protein turnover in steers differing in mature size (1993), unpublished).
†Data obtained from finishing swine experiment (Rathmacher, J. A. et al., "Estimation of 3-methylhistidine production in pigs by compartmental analysis," J. Anim. Sci (1995) In Press).
§Data summarized from Rathmacher, J. A., "Comparative evaluation of muscle proteolysis by a compartmental model of 3-methylhistidine," Ames: Ph. D. Thesis, Iowa State University, 1994.
¶Data obtained from dog experiment (Rathmacher, J. A. et al., "A compartmental model to measure 3-methylhistidine production in dogs following surgery," J. Nutr. (1994) submitted).

TABLE 4-continued

Summary of 3-methylhistidine metabolism
as described by a 3-compartment model.
Included are mass of compartments and mass transfer rates.

| Parameter | Human | Cattle* | Pigs† | Sheep§ | Dogs¶ |
|---|---|---|---|---|---|

Figure 4A:
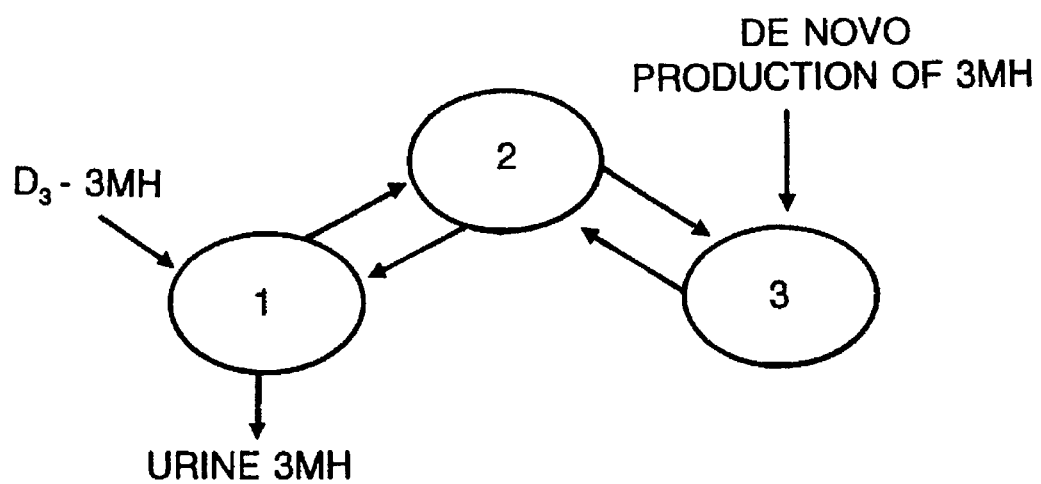
FIG. 4A–C. A comparison of 3-compartment model structures of 3-methylhistidine metabolism among cattle, humans, sheep and swine.
Figure 4B:
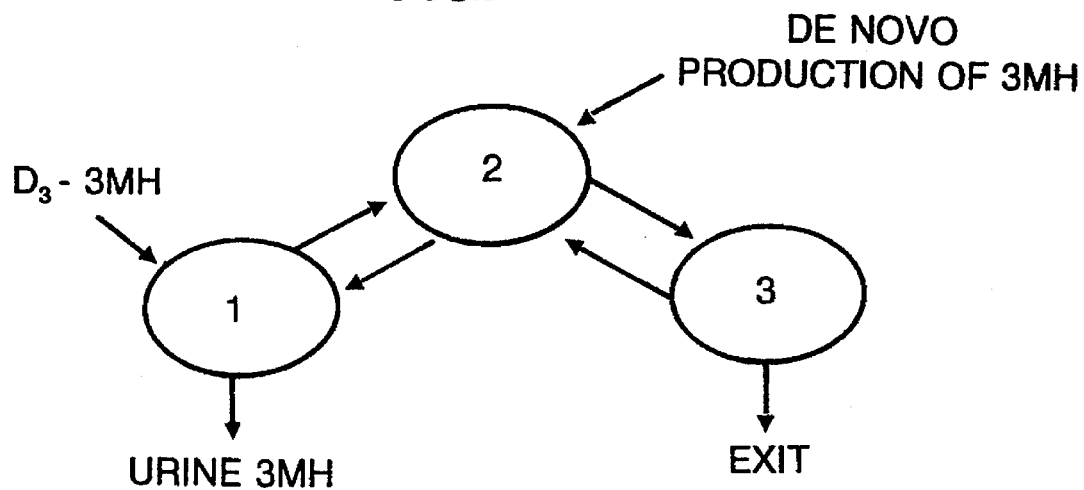
Figure 4C:
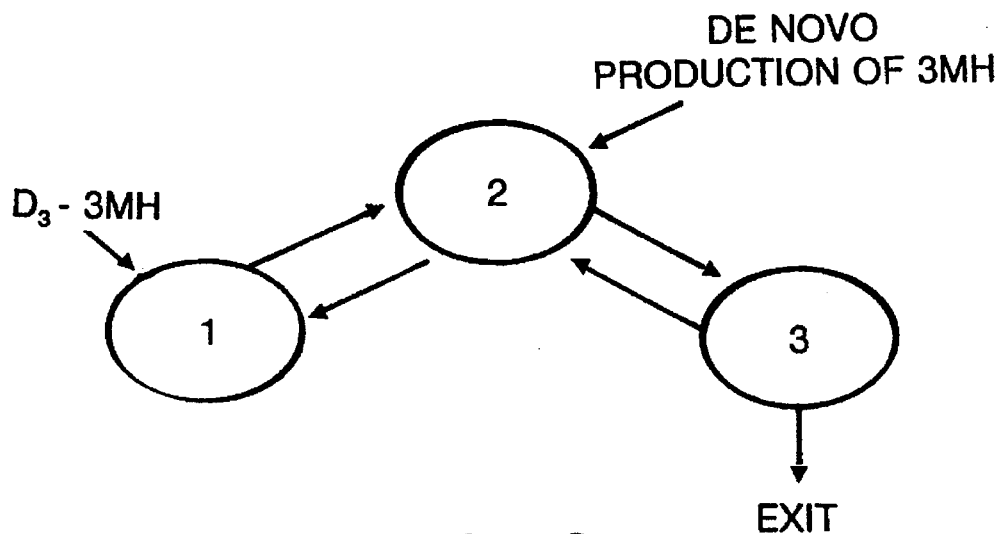

**$M_i$ = compartment mass i; R = mass transfer rate between compartment j and i; 3-methylhistidine production was obtained from the model (See FIG. 4A, 4B, and 4C for model illustration).

Urinary 3-methylhistidine may be used in cattle and humans as an index of muscle protein breakdown but is invalid for use in pigs and lambs. 3-methylhistidine is produced in these species but is not quantitatively excreted in the urine. Previously, in validating urinary 3-methylhistidine as an index of muscle proteolysis, researchers have injected $^{14}$C-3-methylhistidine intravenously and recovered the tracer in urine but have never described its decay in plasma. In constructing the 3-compartment model, we kept in mind known physiology of 3-methylhistidine. It has been established that there are pools of 3-methylhistidine in plasma, in other extracellular fluid pools, within muscle and in other tissues. The primary fate of 3-methylhistidine in humans, cattle and dogs is into urine (model exit from compartment 1), but in sheep and pigs there is a balenine pool in muscle that accumulates over time (model exit from compartment 3). The kinetic data were initially fitted to three exponential terms, indicating the possibility of a three compartment model. Based on these results a series of linear time-invariant compartmental models were constructed. Model code 10 of SAAM was used and the models were based on a set of linear differential equations having constant coefficients. Based on comparison of fits, a 3-compartment model was the best model to describe the metabolism of 3-methylhistidine; however, 2- and 4-compartment models as well as other configurations were also evaluated. A 3-compartment model provided the best fit and was significantly different from a 2-compartment model (P<0.05); there was no advantage to adding a fourth compartment. Next, studies were designed utilizing the decay of a tracer of 3-methylhistidine over a 5-day period. From these data a compartmental model in lambs was developed and a steady state production rate of 3-methylhistidine was estimated. However, with most isotopic models it is difficult to validate them because there are no non-isotopic methods to validate the isotope models. The approach taken to validate the 3-methylhistidine model in sheep was comparative, using species in which urinary 3-methylhistidine is a valid index of muscle proteolysis. Studies in cattle, humans and dogs were used to compare the estimates of 3-methylhistidine as estimated from the model to urinary 3-methylhistidine production.

The major accomplishments of the experiments were: (1) isotopic decay of a tracer of 3-methylhistidine can be described by a 3-compartment model in sheep and pigs where urinary 3-methylhistidine is an invalid index of muscle proteolysis; (2) 3-methylhistidine production as estimated by the model in humans, cattle and dogs was qualitatively similar to urinary 3-methylhistidine production; (3) a minimal 1-compartmental model was developed based on the terminal slope of the model; and (4) model parameters and the steady state compartment mass and fluxes as determined by the model are related to muscle mass.

There are three assumptions that must be accepted when using linear compartmental models. First, the volume or mass of the compartment is assumed to remain constant. Secondly, the compartments are well-stirred; that is, when you sample a compartment, a representative sample of the entire compartment is taken. Finally, the rate constants remain constant. The 3-methylhistidine model in general also has specific assumptions: (1) 3-methylhistidine is not reutilized to a significant extent as there is no tRNA for 3-methylhistidine; (2) the precursor pool does not change; the myofibrillar protein-bound 3-methylhistidine does not change with the experimental conditions. There is some indication that the pool increases shortly after birth. Our data would indicate that neither pharmacological manipulation nor dietary manipulation change the concentration in skeletal muscle. However, there may be some difference between muscles (longissimus dorsi vs. semitendinosus); (3) 3-methylhistidine is quantitatively excreted in the urine or, if metabolic products of free 3-methylhistidine do occur, they are accounted for in the model. This is true for humans, cattle and dogs but not for sheep and pigs. In sheep and pigs a large proportion is retained in muscle as balenine but the model was adjusted to explain this process; (4) renal absorption does not change or is similar between treatments. This may be one explanation why sheep and pigs do not quantitatively excrete 3-methylhistidine in the urine. These species may selectively reabsorb 3-methylhistidine; (5) no 3-methylhistidine in the diet or, if present, 3-methylhistidine calculations must be corrected for dietary 3-methylhistidine; (6) the primary source of 3-methylhistidine is from skeletal muscle myofibrillar protein. This assumption has caused the most controversy between researchers. On an organ basis, skeletal muscle contains more than 90% of the protein-bound 3-methylhistidine.

novo production of 3-methylhistidine could be placed as an entry into compartment 2 and an identical rate calculated. The compartment identity of compartment 2 and 3 is intracellular pools of 3-methylhistidine. The metabolic form of 3-methylhistidine in these compartments may not be identical nor is the identity of compartment 2 or 3 for one species the same identity for another species (i.e., cattle vs. sheep). The models also depict differences in the route by which 3-methylhistidine exits the system. In cattle, humans and dogs, 3-methylhistidine is quantitatively excreted in the urine as illustrated by the exit from compartment 1. This urinary exit has been confirmed by comparison of urinary excretion of 3-methylhistidine and model calculated values, whereas sheep excrete only 15% of total daily 3-methylhistidine produced in the urine and pigs 1.5%/d. Therefore, accurate accounting of 3-methylhistidine production in sheep and pigs requires an exit out of the system from compartment 3. This exit accounts for appreciable loss of 3-methylhistidine into a balenine "sink" which turns over slowly or not at all during the time frame of the study.

In general, each species exhibited a similar exponential decay curve characterized by rapid decay over the first 2–3 hours, followed by a slower decay through 12 hours, and a steady state decay over the remainder of the study. The decays of tracer are representative of the models used. Cattle, humans and dogs exhibit very similar decays while sheep and pigs are very different.

Table 5 lists the model parameters, fractional transfer rates ($L_{ij}$ from compartment j to i). The fractional standard deviation of the parameters ranges from 5 to 50% and in

TABLE 5

Comparison of 3-methylhistidine kinetic parameters.

| Species | Number | Urinary 3MH loss, % of total | Fractional transfer rate, min$^{-1}$* | | | | | |
|---|---|---|---|---|---|---|---|---|
| | | | $L_{2,1}$ | $L_{1,2}$ | $L_{3,2}$ | $L_{2,3}$ | $L_{0,3}$ | $L_{0,1}$ |
| Cattle | 39 | 100 | .18 | .06 | .003 | .002 | NA** | .006 |
| Humans | 4 | 100 | .08 | .06 | .009 | .002 | NA | .004 |
| Dogs | 5 | 100 | .11 | .06 | .006 | .008 | NA | .02 |
| Swine | 20 | 1 | .23 | .09 | .014 | .006 | .0009 | NA |
| Sheep | 40 | 17 | .21 | .08 | .007 | .005 | .0004 | .0003 |

*Fractional transfer rate ($L_{ij}$) from compartment j to i.
**Not Applicable.

Tables 4 and 5 are summaries of the efforts to model 3-methylhistidine metabolism using a 3-compartment model in humans, cattle, and dogs which quantitatively excrete 3-methylhistidine in urine, as compared to sheep and swine which do not quantitatively excrete 3-methylhistidine into urine. FIG. 4 is a comparison of model structures between the species. The diversity of models between cattle, dogs and humans and sheep and pigs reflects differences in known physiology. In each species the tracer is injected into compartment 1 which, based on size (volume and mass), is similar to plasma and extracellular water space. Compartment 1 was the sampling compartment and the compartment from which the steady state calculations were initiated. All models for each species can be resolved by sampling only plasma, except in sheep—the model in FIG. 4 required the sampling of plasma and urine. However, the sheep model can be resolved from plasma kinetics of 3-methylhistidine if the rate of exit from compartment 1 is fixed. From the steady state calculations the de novo production of 3-methylhistidine was obtained into compartment 3 for humans, cattle and dogs and into compartment 2 for sheep and pigs. The de general $L_{2,1}$, $L_{1,2}$ and $L_{0,1}$ or $L_{0,3}$ are solved with a higher precision than $L_{3,2}$ and $L_{2,3}$. Table 4 compares the compartment masses and mass transfer rates between compartments for each species. Also listed is the de novo production rate calculated by the model in Table 4. An important feature of these models is the description of 3-methylhistidine metabolism within the body. The significance of mass transfer rates and compartment sizes is not fully understood. However, the model parameters and mass transfer rates may explain the failure of sheep and swine to quantitatively excrete 3-methylhistidine in the urine. Three mechanisms may explain this failure of sheep and pigs to excrete 3-methylhistidine: (1) 3-methylhistidine transport between the compartments limits the excretion of 3-methylhistidine; (2) 3-methylhistidine is avidly reabsorbed by the kidney; and (3) enzymatic conversion of 3-methylhistidine to balenine is enhanced. In comparison of data from Tables 4 and 5, the low rate of 3-methylhistidine excretion in sheep and swine is not due to impaired transfer of 3-methylhistidine out of and between compartments. Cattle appear to have lower exchange of 3-methylhistidine between tissues despite near quantitative urinary excretion. The most likely reason for sequestering of 3-methylhistidine in sheep and swine is that the kidneys are very efficient in conserving 3-methylhistidine, which in turn increases compartment size and plasma concentration and through mass action could increase the synthesis of balenine.

EXAMPLE 3

Comparison with Minimal Model.

A minimal model using 4–5 measurements and one compartment rather than three was evaluated. In the minimal model the three pools of the 3-compartment model were combined to form one homogeneous pool of 3-methylhistidine, characterized by a de novo production into the body pool and one exit from the model. The kinetic data between 720 and 4320 min was used for the analysis; this time frame corresponds to apparent linear steady state portion of the decay curve. The limitation of the 1-compartment model is the lost ability to described the entire metabolism of 3-methylhistidine. Only the rate of proteolysis and a total pool size can be estimated. Similar results were obtained in dogs when comparing the complete model (3-compartment) to the minimal model. (Rathmacher, J. et al., "The use of compartmental models of 3-methylhistidine flux to evaluate skeletal muscle protein turnover in implanted steers," J. Anim. Sci. (1993) 71:135.) However, in cattle the minimal model estimates of 3-methylhistidine production were 30% higher, but the estimates of 3-methylhistidine production were highly correlated (r=0.93, P 0.0001).

EXAMPLE 4

Prediction of muscle mass from the 3-methylhistidine model.

Figure 5:
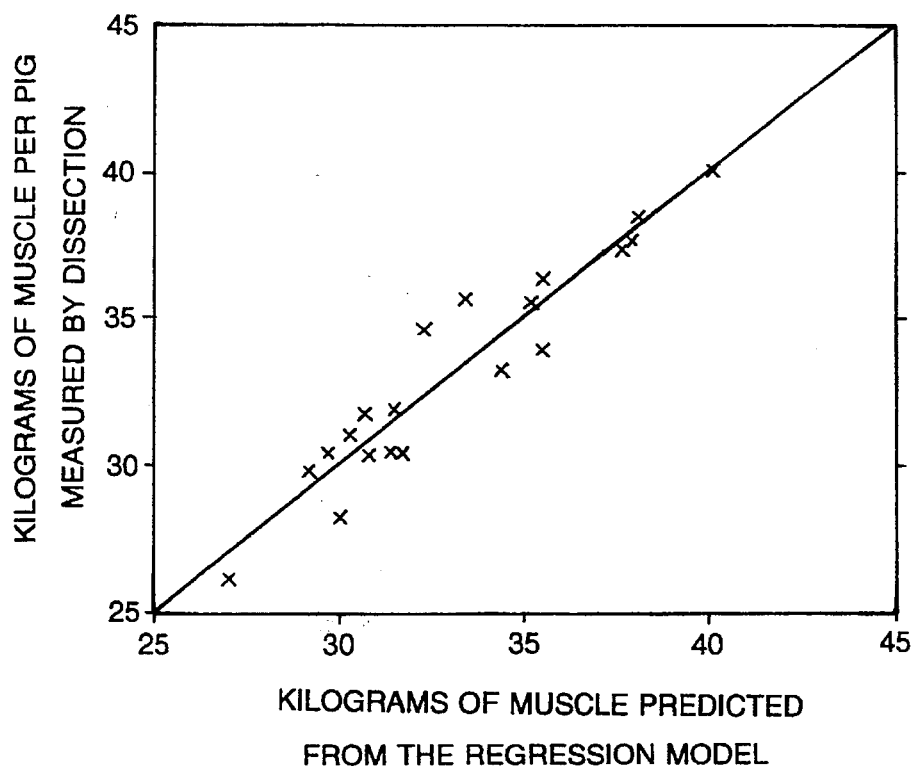
FIG. 5. A plot of muscle mass as predicted by the method of this invention compared to observed muscle mass in swine.
Figure 6:
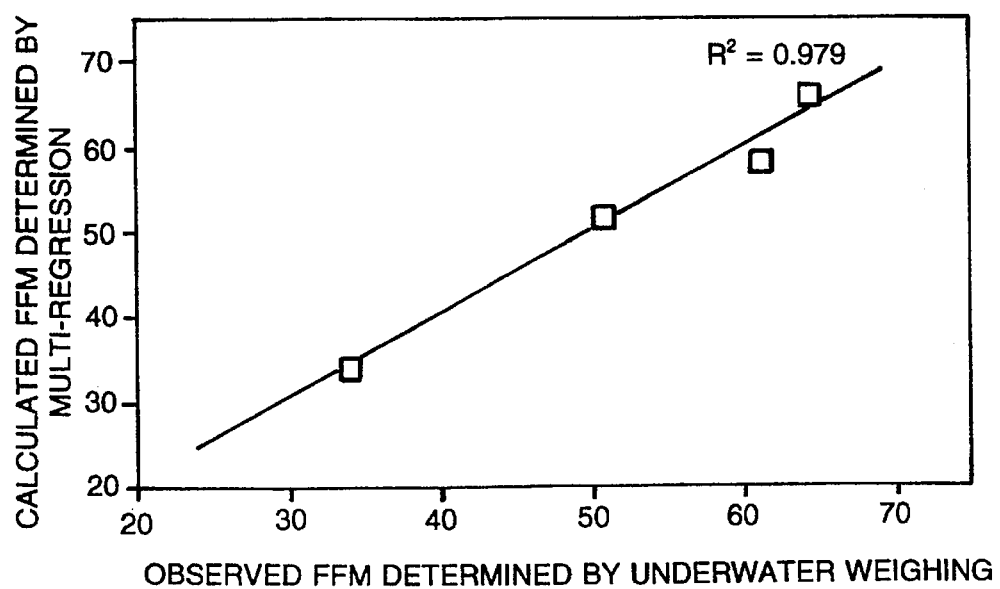
FIG. 6. A plot of fat-free mass determined by the method of this invention as compared to fat free mass as determined by underwater weighing.

From the three-compartment model of 3-methylhistidine metabolism, the model parameters ($L_{ij}$), steady state pool size of these compartments ($M_i$), steady state mass transfer rates ($R_{ij}$), and an estimate of proteolysis ($U_i$) were calculated. The first pool is the compartment where the tracer is introduced and has the volume and mass comparable to plasma plus extracellular fluid. Compartments 2 and 3 are intracellular pools of 3-methylhistidine. Greater than 90% of 3-methylhistidine bound to protein is found in muscle and when the myofibrillar protein is degraded, the 3-methylhistidine enters the tissue compartments. Therefore, the amount of free 3-methylhistidine located in the tissue compartments should be proportional to muscle mass of humans and animals. This relationship would be expected since this compartment is an intracellular pool of free 3-methylhistidine in primarily muscle and as skeletal muscle becomes larger, this pool of 3-methylhistidine should become larger. This relationship would hold true given that the de novo production of 3-methylhistidine, fractional and mass transfer rates, and 3-methylhistidine concentration remained relatively constant. However, this is obviously not true. Therefore, these known variables should be included in any predictive model. This approach has been taken in subsequent analysis of the data in pigs and in humans. In Table 7, we have correlated the compartment mass of a particular species with muscle. In addition, other model parameters have been found to be indicative of muscle mass. In the first example with pigs, the mass of compartment 3 was positively correlated with muscle mass. In addition, the mass transfer rate from compartment 2 to 3 was negatively correlated with muscle mass. The final example for pigs is that the plasma concentration of 3-methylhistidine was negatively correlated to the mass of muscle. Stepwise multiple regression was conducted on model parameters and live body weight to predict muscle mass; variables were added such that $R^2$ was maximized. The $R^2$ was maximized at 0.74 for a 1-variable model and 0.99 for a 12-variable model. A representative model is presented to demonstrate the predictive power of the multiple regression equations. The best 5-variable model is as follows: muscle mass (kg)=−22.7+ 0.117 (plasma 3-methylhistidine, nmol/mL) +0.00000348 (mass of compartment 3, nmol) −0.000903 (mass transfer rate from compartment 2 to 3, nmol/min) +0.263 (weight of the pig) +0.705 (3-methylhistidine production, mol/kg/d) ($R^2$=0.91, P<0.0001). A plot of predicted muscle mass compared to observed muscle mass is presented in FIG. 5. A similar approach was taken with the human data set to predict fat free mass. The model included the variables $M_2$ (compartment mass of pool 2) and $U_3$ (estimate of proteolysis) which is de novo 3-methylhistidine production calculated in the model.

EXAMPLE 5

Prediction of muscle mass in humans using model parameters of a 3-compartment model of 3-methylhistidine.

Eight human volunteers were studied: 3 females and 5 males, age 24.9±2.9 years (range 22.0–31.0), weight 69.1±11.2 kg (range 48.4 to 80.6). Subjects were given an intravenous dose of 3-[methyl-$^2H_3$]-methylhistidine (0.2 µmol/kg of body weight), which was followed by serial blood samples at 1, 2, 5, 10, 30, 45, 90, 150, 210, 330, 510, 720, 1440, 2880 and 4320 min postinjection. Subjects were studied at State University of New York, Stonybrook, Stonybrook Health Sciences Center, School of Medicine, Department of Surgery, Stonybrook, N.Y.

The tracer to tracee ratio and the concentration of 3-methylhistidine was determined by GC/MS as previously described. The kinetic data were modeled according to the previously described 3-compartment model. Results of the modeling are set forth in Table 8. Muscle mass (kg) was determined by prompt gamma neutron-activation at the Medical Research Center, Brookhaven National Laboratory, Upton, N.Y. These data were used in a multiple regression procedure (stepwise multiple procedure of SAS) in which $R^2$ was maximized.

TABLE 7

Relationship between model compartments and muscle.

| Correlation | Correlation coefficient r | P-value |
| --- | --- | --- |
| $M_3$ vs. kg of muscle, pigs | 0.59 | 0.006 |
| $R_{3,2}$ vs. kg of muscle, pigs | −0.64 | 0.002 |
| Plasma 3MH vs. kg of muscle, pigs | −0.52 | 0.02 |
| Multiple regression model vs. kg muscle, pigs | 0.95 | 0.0001 |
| $M_2$ vs. muscle, humans | 0.91 | 0.09 |
| $M_3$ vs. muscle, humans | 0.56 | 0.44 |
| $U_3$ vs. muscle, humans | 0.74 | 0.026 |
| $L_{2,1}$ vs. muscle, humans | −0.92 | 0.08 |
| Multiple regression model vs. muscle, humans | 0.98 | 0.1 |

TABLE 8

Simple Statistics

| Variable | Mean | Standard Deviation | Sum | Minimum | Maximum |
|---|---|---|---|---|---|
| SUBJECT* | 394645 | 101746 | 3157161 | 150500 | 455482 |
| $L_{2,1}$ | 0.137550 | 0.146025 | 1.100400 | 0.024300 | 0.465000 |
| $L_{1,2}$ | 0.043750 | 0.025129 | 0.350000 | 0.014900 | 0.090800 |
| $L_{0,1}$ | 0.007225 | 0.002689 | 0.057800 | 0.003700 | 0.011100 |
| $L_{3,2}$ | 0.011700 | 0.015649 | 0.093600 | 0.002400 | 0.049800 |
| $L_{2,3}$ | 0.003525 | 0.004902 | 0.028200 | 0.001200 | 0.015600 |
| $K_1$ | 0.000149 | 0.000165 | 0.001189 | 0.00001500 | 0.000534 |
| $M_1$ | 35245 | 33508 | 281989 | 10659 | 115608 |
| $M_2$ | 73666 | 33676 | 589327 | 55180 | 154965 |
| $M_3$ | 329564 | 89216 | 2636515 | 254826 | 521745 |
| $U_3$ | 200.575000 | 97.695857 | 1604.600000 | 93.400000 | 422.300000 |
| $R_{2,1}$ | 2762.037500 | 1423.987078 | 22096 | 687.500000 | 4956.000000 |
| $R_{1,2}$ | 2962.600000 | 1427.916643 | 23701 | 824.100000 | 5049.400000 |
| $R_{0,1}$ | 200.575000 | 97.694857 | 1604.600000 | 93.400000 | 422.300000 |
| $R_{3,2}$ | 1293.637500 | 2598.424656 | 10349 | 182.400000 | 7714.000000 |
| $R_{2,3}$ | 1494.200000 | 2687.774951 | 11954 | 360.700000 | 8136.300000 |
| MUSC | 23.450000 | 9.283780 | 187.600000 | 9.000000 | 32.600000 |
| LBM | 59.150000 | 13.041691 | 473.200000 | 38.400000 | 72.600000 |
| $PL_3MH$ | 2.961250 | 1.673768 | 23.690000 | 1.290000 | 5.690000 |
| WT | 69.137500 | 11.134494 | 553.100000 | 48.400000 | 80.600000 |

*N = 8
$L_{ij}$ = Fractional transfer rate from compartment j to i.
$K_i$ = Proportionality c
$M_i$ = Mass of 3-methylhistidine in compartment i (nmol).
$U_i$ = de novo 3-methylhistidine production (nmol · min) from compartment i to j (nmol · min),
MUSC = skeletal muscle calculated as follows: (19.25 TBK-TBN)/38.34
TBN = Total body nitrogen
TBK = Total body potassium
LBM = Lean body mass (Fat Free)
$PL_3MH$ = Plasma 3-methylhistidine concentration (mmol · mL).
WT = Body weight (kg)

Stepwise multiple regression was computed by using the above variables supplied from the 3-compartment model of 3-methylhistidine metabolism; regression models ranged from 1- to 7 variable models with $R^2$ from 0.91 to 0.99, respectively. Muscle in humans can be predicted with a high degree of accuracy (standard error of 0.28 kg). For example:

A 2-variable model used was: Muscle (kg)=−37.86+0.95 (wt) −0.00183($R_{2,1}$) (P=0.0003, $R^2$=0.96);

A 3-variable model used was: Muscle (kg)=−40.76+1.08 (wt)−607.71 ($L_{0,1}$)−0.002($R_{1,2}$) (P=0.001, $R^2$=0.98);

A 4-variable model used was: Muscle (kg)=−39.52+1.10 (wt)+15.82($L_{2,1}$)−884.81($L_{0,1}$)−0.003($R_{2,1}$) (P=0.002, $R^2$=0.99);

A 5-variable model used was: Muscle (kg)=−30.88−31.94 ($L_{2,1}$)+467.78 ($L_{3,2}$)+1.08 (wt)−0.095 ($U_3$)−0.00122 ($R_{2,1}$) (P=0.005, $R^2$=0.99);

A 6-variable model used was: Muscle (kg)=−33.50+1.13 (wt)−23.01 ($L_{2,1}$)−373.03 ($L_{0,1}$)+365.28 ($L_{3,2}$)+0.0744 ($R_{2,1}$)−0.0760($R_{1,2}$) (P=0.01, $R^2$=99);

A 7-variable model used was: Muscle (kg)=−29.89+1.16 (wt)−14.58($L_{2,1}$)−757.97($L_{0,1}$)+374.53($L_{3,2}$)−0.0000175($M_3$)+0.063($R_{2,1}$)−0.065($R_{1,2}$).

The variables are defined as in Table 8.

Table 9 sets forth the regression models showing maximum $R^2$ improvement for the dependent variables.

Table 10 sets forth a representative 5-variable model in detail.

TABLE 9

Regression Models
Maximum $R^2$ Improvement for Dependent Variables

Best 1-variable model found:

| Step 1 | Variable wt entered | | R-square = 0.91830548 | | |
|---|---|---|---|---|---|
| | DF | Sum of Squares | Mean Square | F | Prob > F |
| Regression | 1 | 554.03206417 | 554.03206417 | 67.44 | 0.0002 |
| Error | 6 | 49.28793583 | 8.21465597 | | |
| Total | 7 | 603.32000000 | | | |

| Variable | Parameter Estimate | Standard Error | Type II Sum of Squares | F | Prob > F |
|---|---|---|---|---|---|
| INTERCEP | −31.79100899 | 6.80239450 | 179.42145497 | 21.84 | 0.0034 |
| WT | 0.79900212 | 0.09729156 | 554.03206417 | 67.44 | 0.0002 |

Bounds on condition number: 1, 1

TABLE 9-continued

Regression Models
Maximum $R^2$ Improvement for Dependent Variables

Best 2-variable model found:

Step 2  Variable $R_{2,1}$ entered    R-square = 0.95996839

| | DF | Sum of Squares | Mean Square | F | Prob > F |
|---|---|---|---|---|---|
| Regression | 2 | 579.16812909 | 289.58406455 | 59.95 | 0.0003 |
| Error | 5 | 24.15187091 | 4.83037418 | | |
| Total | 7 | 603.30000000 | | | |

| Variable | Parameter Estimate | Standard Error | Type II Sum of Squares | F | Prob > F |
|---|---|---|---|---|---|
| INTERCEP | −37.85625493 | 5.85478579 | 201.94543925 | 41.81 | 0.0013 |
| WT | 0.95988723 | 0.10266494 | 422.25705563 | 87.42 | 0.0002 |
| $R_{2,1}$ | −0.00183124 | 0.00080276 | 25.13606493 | 5.20 | 0.0714 |

Bounds on condition number: 1.893662, 7.57465

Best 3-variable model found:

Step 3  Variable wt entered    R-square = 0.97321964

| | DF | Sum of Squares | Mean Square | F | Prob > F |
|---|---|---|---|---|---|
| Regression | 3 | 587.16287041 | 195.72095680 | 48.45 | 0.0013 |
| Error | 4 | 16.15712959 | 4.03928240 | | |
| Total | 7 | 603.32000000 | | | |

| Variable | Parameter Estimate | Standard Error | Type II Sum of Squares | F | Prob > F |
|---|---|---|---|---|---|
| INTERCEP | −40.42035822 | 5.65564778 | 206.31928473 | 51.08 | 0.0020 |
| WT | 1.06061831 | 0.11806973 | 325.94576397 | 80.69 | 0.0008 |
| $L_{0,1}$ | −530.48875532 | 377.07356166 | 7.99474132 | 1.98 | 0.2322 |
| $R_{2,1}$ | −0.00203667 | 0.00074847 | 29.90861018 | 7.40 | 0.0529 |

Bounds on condition number: 2.995104, 20.23609

Step 4  Variable $R_{2,1}$ Removed    R-square = 0.97635829
        Variable $R_{1,2}$ Entered

| | DF | Sum of Squares | Mean Square | F | Prob > F |
|---|---|---|---|---|---|
| Regression | 3 | 589.05648123 | 196.35216041 | 55.06 | 0.0010 |
| Error | 4 | 14.26351877 | 3.56587969 | | |
| Total | 7 | 603.32000000 | | | |

| Variable | Parameter Estimate | Standard Error | Type II Sum of Squares | F | Prob > F |
|---|---|---|---|---|---|
| INTERCEP | −40.75748032 | 5.33097710 | 208.43358964 | 58.45 | 0.0016 |
| WT | 1.08399144 | 0.11469893 | 318.49282168 | 89.32 | 0.0007 |
| $L_{0,1}$ | −607.70936499 | 359.68195412 | 10.17937811 | 2.85 | 0.1664 |
| $R_{1,2}$ | −0.00214213 | 0.00071730 | 31.80222100 | 8.92 | 0.0405 |

Bounds on condition number: 3.201777, 21.29248

Best 4-variable model found:

Step 5  Variable $L_{2,1}$ Entered    R-square = 0.99070888

| | DF | Sum of Squares | Mean Square | F | Prob > F |
|---|---|---|---|---|---|
| Regression | 4 | 597.71448196 | 149.42862049 | 79.97 | 0.0022 |
| Error | 3 | 5.60551804 | 1.86850601 | | |
| Total | 7 | 603.32000000 | | | |

| Variable | Parameter Estimate | Standard Error | Type II Sum of Squares | F | Prob > F |
|---|---|---|---|---|---|
| INTERCEP | −39.81660277 | 3.88363891 | 196.40168878 | 105.11 | 0.0020 |
| WT | 1.12191046 | 0.08487587 | 326.46931089 | 174.72 | 0.0009 |
| $L_{2,1}$ | 13.30894179 | 6.18275399 | 8.65800073 | 4.63 | 0.1204 |
| $L_{0,1}$ | −933.37777826 | 301.12952196 | 17.95158271 | 9.61 | 0.0533 |
| $R_{1,2}$ | −0.00316832 | 0.00070489 | 37.74934146 | 20.20 | 0.0206 |

Bounds on condition number: 3.795361, 50.6051

Step 6  Variable $R_{1,2}$ Removed    R-square = 0.99124272
        Variable $R_{2,1}$ Entered

| | DF | Sum of Squares | Mean Square | F | Prob > F |
|---|---|---|---|---|---|
| Regression | 4 | 598.03655751 | 149.50913938 | 84.89 | 0.0020 |

TABLE 9-continued

Regression Models
Maximum $R^2$ Improvement for Dependent Variables

| | | | | |
|---|---|---|---|---|
| Error | 3 | 5.28344249 | 1.76114750 | |
| Total | 7 | 603.32000000 | | |

| Variable | Parameter Estimate | Standard Error | Type II Sum of Squares | F | Prob > F |
|---|---|---|---|---|---|
| INTERCEP | −39.52297300 | 3.75188492 | 195.43211079 | 110.97 | 0.0018 |
| WT | 1.10403918 | 0.07989664 | 336.28510239 | 190.95 | 0.0008 |
| $L_{2,1}$ | 15.82428846 | 6.36844848 | 10.87368710 | 6.17 | 0.0889 |
| $L_{0,1}$ | −884.81980507 | 286.92825809 | 16.74783817 | 9.51 | 0.0540 |
| $R_{2,1}$ | −0.00330964 | 0.00071183 | 38.07141701 | 21.62 | 0.0188 |

Bounds on condition number: 4.083871, 52.13148
Best 5-variable model found:

Step 7  Variable $L_{3,2\ Entered}$  R-square = 0.99297290

| | DF | Sum of Squares | Mean Square | F | Prob > F |
|---|---|---|---|---|---|
| Regression | 5 | 599.08041113 | 119.81608223 | 56.52 | 0.0175 |
| Error | 2 | 4.23958887 | 2.11979443 | | |
| Total | 7 | 603.32000000 | | | |

| Variable | Parameter Estimate | Standard Error | Type II Sum of Squares | F | Prob > F |
|---|---|---|---|---|---|
| INTERCEP | −37.74782987 | 4.83139648 | 129.39943165 | 61.04 | 0.0160 |
| WT | 1.04849249 | 0.11810649 | 167.06168405 | 78.81 | 0.0125 |
| $L_{2,1}$ | 18.26175636 | 7.80265839 | 11.61164232 | 5.48 | 0.1441 |
| $L_{0,1}$ | −656.36183687 | 452.86183565 | 4.45296156 | 2.10 | 0.2843 |
| $L_{3,2}$ | 47.42509768 | 67.58266413 | 1.04385362 | 0.49 | 0.5555 |
| $R_{2,1}$ | −0.00348181 | 0.00081859 | 38.35031346 | 18.09 | 0.0511 |

Bounds on condition number: 5.710746, 115.3744
Step 8  Variable $L_{0,1}$ Removed   R-square = 0.99795894
        Variable $U_3$ Entered

| | DF | Sum of Squares | Mean Square | F | Prob > F |
|---|---|---|---|---|---|
| Regression | 5 | 602.08858510 | 120.41771702 | 195.58 | 0.0051 |
| Error | 2 | 1.23141490 | 0.61570745 | | |
| Total | 7 | 603.32000000 | | | |

| Variable | Parameter Estimate | Standard Error | Type II Sum of Squares | F | Prob > F |
|---|---|---|---|---|---|
| INTERCEP | −30.88073963 | 2.42520239 | 99.82833369 | 162.14 | 0.0061 |
| WT | 1.08775288 | 0.06337577 | 181.37956823 | 294.59 | 0.0034 |
| $L_{2,1}$ | −31.93939487 | 15.05496627 | 2.77120212 | 4.50 | 0.1679 |
| $L_{3,2}$ | 467.77525419 | 103.66319961 | 12.53717468 | 20.36 | 0.0458 |
| $U_3$ | −0.09259734 | 0.02660010 | 7.46113553 | 12.12 | 0.0735 |
| $R_{2,1}$ | −0.00122401 | 0.00075528 | 1.61706341 | 2.63 | 0.2465 |

Bounds on condition number: 76.77743, 902.2671
Best 6-variable model found:

Step 9  Variable $L_{0,1}$ Entered   R-square = 0.99994505

| | DF | Sum of Squares | Mean Square | F | Prob > F |
|---|---|---|---|---|---|
| Regression | 6 | 603.28684838 | 100.54780806 | 3032.97 | 0.0139 |
| Error | 1 | 0.03315162 | 0.03315162 | | |
| Total | 7 | 603.32000000 | | | |

| Variable | Parameter Estimate | Standard Error | Type II Sum of Squares | F | Prob > F |
|---|---|---|---|---|---|
| INTERCEP | −33.50363960 | 0.71205189 | 73.39481615 | 2213.91 | 0.0135 |
| WT | 1.13428105 | 0.01661790 | 154.45216308 | 4658.96 | 0.0093 |
| $L_{2,1}$ | −23.03887764 | 3.79412210 | 1.22237575 | 36.87 | 0.1039 |
| $L_{0,1}$ | −372.63876382 | 61.98180975 | 1.19826329 | 36.14 | 0.1049 |
| $L_{3,2}$ | 365.42672310 | 29.46884753 | 5.09775549 | 153.77 | 0.0512 |
| $U_3$ | −0.07609328 | 0.00675525 | 4.20643725 | 126.88 | 0.0564 |
| $R_{2,1}$ | −0.00167249 | 0.00019047 | 2.55605769 | 77.10 | 0.0722 |

Bounds on condition number: 91.96439, 1381.858
Step 10  Variable $U_3$ Removed   R-square = 0.99994858

TABLE 9-continued

Regression Models
Maximum $R^2$ Improvement for Dependent Variables

Variable $R_{1,2}$ Entered

| | DF | Sum of Squares | Mean Square | F | Prob > F |
|---|---|---|---|---|---|
| Regression | 6 | 603.28897530 | 100.54816255 | 3240.91 | 0.0134 |
| Error | 1 | 0.03102470 | 0.03102470 | | |
| Total | 7 | 603.32000000 | | | |

| Variable | Parameter Estimate | Standard Error | Type II Sum of Squares | F | Prob > F |
|---|---|---|---|---|---|
| INTERCEP | −33.49983500 | 0.68895580 | 73.35170746 | 2634.30 | 0.0131 |
| WT | 1.13413092 | 0.01606923 | 154.54113534 | 4981.23 | 0.0090 |
| $L_{2,1}$ | −23.01024937 | 3.66715320 | 1.22149631 | 39.37 | 0.1006 |
| $L_{0,1}$ | −373.02799394 | 59.94449237 | 1.20141180 | 38.72 | 0.1014 |
| $L_{3,2}$ | 365.27810472 | 28.48902405 | 5.10034736 | 164.40 | 0.0496 |
| $L_{2,1}$ | 0.07437503 | 0.00668546 | 3.83971895 | 123.76 | 0.0571 |
| $R_{1,2}$ | −0.07604852 | 0.00652946 | 4.20856417 | 135.65 | 0.0545 |

Bounds on condition number: 20448.67, 241107.8
Best 7-variable model found.

Step 11   Variable $M_3$ Entered      R-square = 1.0000000

| | DF | Sum of Squares | Mean Square | F | Prob > F |
|---|---|---|---|---|---|
| Regression | 7 | 603.32000000 | 86.18857143 | . | . |
| Error | 0 | 0.00000000 | . | | |
| Total | 7 | 603.32000000 | | | |

| Variable | Parameter Estimate | Standard Error | Type II Sum of Squares | F | Prob > F |
|---|---|---|---|---|---|
| INTERCEP | −29.89167712 | . | 2.05439877 | . | . |
| WT | 1.15634509 | . | 55.18791951 | . | . |
| $L_{2,1}$ | −14.58369649 | . | 0.07813012 | . | . |
| $L_{0,1}$ | −757.96529705 | . | 0.11744110 | . | . |
| $L_{3,2}$ | 374.52514588 | . | 4.85079707 | . | . |
| $M_3$ | −0.00001745 | . | 0.03102470 | . | . |
| $R_{2,1}$ | 0.06284371 | . | 0.68964461 | . | . |
| $R_{1,2}$ | −0.06458185 | . | 0.74316320 | . | . |

Bounds on condition number: 81284.64, 1138603
No further improvement in R-square is possible.

TABLE 10

Representative 5-variable model.

Analysis of Variance

| Source | DF | Sum of Squares | Mean Square | F Value | Prob > F |
|---|---|---|---|---|---|
| Model | 5 | 602.08859 | 120.41772 | 195.576 | 0.0051 |
| Error | 2 | 1.23141 | 0.61571 | | |
| C Total | 7 | 603.32000 | | | |

| | | | |
|---|---|---|---|
| Root MSE | 0.78467 | R-square | 0.9980 |
| Dep Mean | 23.45000 | Adj R-sq | 0.9929 |
| C.V. | 3.34614 | | |

Parameter Estimates

| Variable | DF | Parameter Estimate | Standard Error | T for HO: Parameter = 0 | Prob > |T| |
|---|---|---|---|---|---|
| INTERCEP | 1 | −30.880740 | 2.42520239 | −12.733 | 0.0061 |
| $L_{2,1}$ | 1 | −31.939395 | 15.05496627 | −2.122 | 0.1679 |
| $L_{3,2}$ | 1 | 467.775254 | 103.66319961 | 4.512 | 0.0458 |
| $U_3$ | 1 | −0.092597 | 0.02660010 | −3.481 | 0.0735 |
| $R_{2,1}$ | 1 | −0.001224 | 0.00075528 | −1.621 | 0.2465 |
| WT | 1 | 1.087753 | 0.06337577 | 17.164 | 0.0034 |

Dep Var   Predict   Std Err   Lower 95%   Upper 95%   Lower 95%   Upper 95%

TABLE 10-continued

Representative 5-variable model.

| Obs | MUSC | Value | Predict | Mean | Mean | Predict | Predict | Residual |
|---|---|---|---|---|---|---|---|---|
| 1 | 14.4000 | 14.6090 | 0.768 | 11.3046 | 17.9135 | 9.8849 | 19.3332 | −0.2090 |
| 2 | 27.2000 | 27.1574 | 0.781 | 23.7979 | 30.5168 | 22.3946 | 31.9202 | 0.0426 |
| 3 | 28.5000 | 29.0651 | 0.634 | 26.3355 | 31.7947 | 24.7236 | 33.4067 | −0.5651 |
| 4 | 30.1000 | 29.7929 | 0.654 | 26.9789 | 32.6069 | 25.3978 | 34.1880 | 0.3071 |
| 5 | 31.4000 | 31.4522 | 0.470 | 29.4301 | 33.4743 | 27.5168 | 35.3876 | −0.0522 |
| 6 | 32.6000 | 32.4646 | 0.769 | 29.1539 | 35.7753 | 27.7361 | 37.1931 | 0.1354 |
| 7 | 9.0000 | 9.4179 | 0.726 | 6.2962 | 12.5397 | 4.8197 | 14.0162 | −0.4179 |
| 8 | 14.4000 | 13.6407 | 0.570 | 11.1869 | 16.0946 | 9.4670 | 17.8144 | 0.7593 |

| | |
|---|---|
| Sum of Residuals | 0 |
| Sum of Squared Residuals | 1.2314 |
| Predicted Resid SS (Press) | 70.3390 |

This invention has been described with respect to specific embodiments. Equivalent methods to those described will be readily apparent to those skilled in the art and are included within the scope of the appended claims.

We claim:

1. A method for determining muscle mass in a human subject comprising:
   (a) administering to said subject a known amount of a metabolic marker for 3-methylhistidine;
   (b) periodically removing blood or urine samples from said subject;
   (c) measuring the amount of said marker and of 3-methylhistidine in each such sample;
   (d) generating a three-compartment mathematical model from said measurements comprising numerical values for the fractional transfer rates in and out of said compartments, numerical values for the mass of 3-methylhistidine in each compartment, and numerical values for the mass transfer rates in and out of said compartments;
   (e) calculating muscle mass as a function of the numerical value of at least one of said values and the total body weight of the subject.

2. The method of claim 1 wherein total body weight of the subject is obtained and muscle mass is calculated as a function of total body weight and the numerical value of compartment 2.

3. The method of claim 1 wherein muscle mass is calculated as a function of the numerical value of the mass of 3-methylhistidine in compartment 2, and of the fractional transfer rate between compartment 1 of said model and urine.

4. The method of claim 1 wherein total body weight of the subject is obtained and muscle mass is calculated as a function of total body weight, the numerical value of the mass of 3-methylhistidine in compartment 2, and the fractional transfer rate between compartment 1 of said model and urine.

5. The method of claim 1 wherein total body weight of the subject is obtained and muscle mass is calculated as a function of total body weight, the mass of 3-methylhistidine in compartment 2, the fractional transfer rate between compartment 1 of said model into urine, and the mass transfer rate from compartment 2 to compartment 1.

6. The method of claim 1 wherein total body weight of the subject is obtained and muscle mass is calculated as a function of total body weight, the fractional transfer rate between compartments 2 and 1, the fractional transfer rate between compartment 1 of said model into urine, the mass of 3-methylhistidine in compartment 1, and the mass transfer rate between compartments 3 and 2.

7. The method of claim 1 wherein said marker is $D_3$-methylhistidine.

8. The method of claim 1 wherein said marker is administered in an amount between about 0.2 nmol/kg body weight and about 0.8 nmol/kg body weight.

9. The method of claim 1 wherein said marker is administered intravenously.

10. The method of claim 1 wherein said marker is administered orally.

11. The method of claim 1 wherein said blood or urine samples are taken over the period required to substantially reach steady state.

12. The method of claim 1 wherein said blood or urine samples are taken over a period of between about 48 and about 72 hours.

13. The method of claim 1 wherein at least about 14 said blood or urine samples are taken.

14. The method of claim 1 wherein said amounts of marker and 3-methylhistidine are measured by gas chromatography mass spectroscopy.

15. The method of claim 1 wherein said mathematical model is generated using the SAAM computer program.

16. The method of claim 2 wherein said calculation of muscle mass as a function of mass of 3-methylhistidine in compartment 2 and body weight is made using the equation:

$$\text{Muscle mass (kg)} = -31.96 + 0.0000027(M_2) + 0.80 \text{ (wt)}$$

where $M_2$ = the mass of 3-methylhistidine in compartment 2 (nmol) and wt = body weight (kg).

17. The method of claim 3 wherein said calculation of muscle mass is made as a function of both the numerical value of 3-methylhistidine in compartment 2 and of the fractional transfer rate between compartment 1 of said model and urine using the equation:

$$\text{Muscle mass (kg)} = -9.90 + 3039.5(L_{0,1}) + 0.000155(M_2)$$

where $L_{0,1}$ = the fractional transfer rate from compartment 1 into urine (min$^{-1}$) and $M_2$ = the mass of 3-methylhistidine in compartment 2 (nmol).

18. The method of claim 4 wherein said calculation of muscle mass is made as a function of total body weight of the subject, the mass of 3-methylhistidine in compartment 2, and the fractional transfer rate between compartment 1 of said model and urine using the equation:

Muscle mass (kg)=−32.39−0.00035($M_2$)−783.194($L_{0,1}$)+0.927 (Wt)

where $M_2$=the mass of 3-methylhistidine in compartment 2 (nmol), $L_{0,1}$=the fractional transfer rate of compartment 1 into urine (min$^{-1}$) and wt=body weight (kg).

19. The method of claim 5 wherein said calculation of muscle mass is made as a function of total body weight, the mass of 3-methylhistidine in compartment 2, the fractional transfer rate between compartment 1 of said model into urine, and the mass transfer rate from compartment 2 to compartment 1, using the equation:

Muscle mass (kg)=−40.16−0.000031($M_2$)−1000.69($L_{0,1}$)−0.0021($R_{1,2}$)+1.15 (wt)

where $M_2$=the mass of 3-methylhistidine in compartment 2 (nmol), $L_{0,1}$=the fractional transfer rate between compartment 1 of said model into urine (min$^{-1}$), $R_{1,2}$=the mass transfer rate from compartment 2 to compartment 1 (min$^{-1}$ $^1$), and wt=body weight (kg).

20. The method of claim 6 wherein said calculation of muscle mass is made as a function of total body weight, the mass of 3-methylhistidine in compartment 1, the fractional transfer rate between compartments 2 and 1, the fractional transfer rate between compartment 1 and urine, and the mass transfer rate between compartments 3 and 2, using the equation:

Muscle mass (kg)=−22.02−255.13($L_{1,2}$)−2498.4($L_{0,1}$)−0.000579($M_1$)+0.00486($R_{2,3}$)+1.27 (wt)

where $L_{1,2}$=the fractional transfer rate between compartments 2 and 1 (min$^{-1}$), $L_{0,1}$=the fractional transfer rate from compartment 1 into urine (min$^{-1}$), $M_1$=the mass of 3-methylhistidine in compartment 1 (nmol), $R_{2,3}$=the mass transfer rate between compartments 3 and 2, and wt=body weight (kg).

* * * * *

UNITED STATES PATENT AND TRADEMARK OFFICE
CERTIFICATE OF CORRECTION

PATENT NO. : 5,628,328

DATED : May 13, 1997

INVENTOR(S) : Nissen et al.

It is certified that error appears in the above-indentified patent and that said Letters Patent is hereby corrected as shown below:

In Column 1, lines 3-6, delete "This invention was made, at least in part, with funding from the National Institutes of Health (Grants DK-26657, DK-20593, RR-00095 and DK-43290) and the United States Government may have certain rights therein."

In Column 1, line 31, delete "Of" and replace with --Of--.

In Column 3, line 19, delete "interindividual" and replace with --inter-individual--.

In Column 7, line 41, delete the space which appears before "$^2H_3$-methyl".

In Column 7, line 42, delete "$_{13}C$" and replace with --$^{13}C$--.

In Column 12, line 49, delete "$\mu mol\text{-}kg^{-1}\cdot d^{-1}$" and replace with --$\mu mol\cdot kg^{-1}\cdot d^{-1}$--.

In Column 12, line 50, delete "$\mu mol\cdot mg^-$" and replace with --$\mu mol\cdot mg^{-1}$--.

In Column 12, line 51, delete "1).".

In Column 14, Table 2, last line of "Mean" column, delete "19.63" and replace with --9.63--.

In Column 15, Table 4, final line under "parameter" column, delete "$\mu mol\cdot kg^{-1}.d^{-1}$" and replace with --$\mu mol\cdot kg^{-1}\cdot d^{-1}$--.

In Column 21, Table 8, fourth line of "Mean" column, delete "0.00722S" and replace with --0.007225--.

In Column 21, Table 8, eighth line of "Sum" column, delete "2819S9" and replace with --281959--.

In Column 23 (Table 9-continued) line 9, delete "603.30000000" and replace with --603.32000000--.

UNITED STATES PATENT AND TRADEMARK OFFICE
CERTIFICATE OF CORRECTION

PATENT NO. : 5,628,328

DATED : May 13, 1997

INVENTOR(S) : Nissen et al.

It is certified that error appears in the above-indentified patent and that said Letters Patent is hereby corrected as shown below:

In Column 31, line 22, delete "$min^{-1\ 1}$" and replace with --$min^{-1}$--.

Signed and Sealed this

Twenty-first Day of October 1997

Attest:

BRUCE LEHMAN

*Attesting Officer*   *Commissioner of Patents and Trademarks*